(12) United States Patent
Ishikawa et al.

(10) Patent No.: US 12,367,618 B2
(45) Date of Patent: Jul. 22, 2025

(54) INFORMATION PROCESSING DEVICE, INFORMATION PROCESSING METHOD, INFORMATION PROCESSING PROGRAM, AND INFORMATION PROCESSING SYSTEM

(71) Applicant: NIKON CORPORATION, Tokyo (JP)

(72) Inventors: Momotaro Ishikawa, Tokyo (JP); Toshihide Tadaki, Tokyo (JP); Takeyuki Abe, Tokyo (JP); Kohma Hayashi, Tokyo (JP); Kyoko Negishi, Tokyo (JP); Ryoko Sendoda, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 17/763,831

(22) PCT Filed: Sep. 27, 2019

(86) PCT No.: PCT/JP2019/038163
§ 371 (c)(1),
(2) Date: Aug. 15, 2022

(87) PCT Pub. No.: WO2021/059487
PCT Pub. Date: Apr. 1, 2021

(65) Prior Publication Data
US 2024/0290004 A1    Aug. 29, 2024

(51) Int. Cl.
*G06T 11/00* (2006.01)
*G06T 7/40* (2017.01)
(Continued)

(52) U.S. Cl.
CPC ......... *G06T 11/001* (2013.01); *G06V 20/698* (2022.01)

(58) Field of Classification Search
CPC .......... G06T 11/00; G06T 2207/30024; G06T 7/0016; G06T 7/40; G06T 7/80;
(Continued)

(56) References Cited

U.S. PATENT DOCUMENTS 7,047,550 B1 * 5/2006 Yasukawa .......... H04N 21/6582
                                                  725/50
7,315,985 B1 * 1/2008 Gauvin ................ H04L 41/12
                                                  715/764
(Continued)

FOREIGN PATENT DOCUMENTS

CN    108021601 B  * 12/2023 ........... G06F 16/532
JP    2013-137635 A    7/2013
(Continued)

OTHER PUBLICATIONS

May 30, 2023 Office Action issued in Japanese Patent Application No. 2021-548121.
(Continued)

*Primary Examiner* — Wesner Sajous
(74) *Attorney, Agent, or Firm* — Oliff PLC

(57) ABSTRACT

An information processing device includes: an acquirer that acquires observation results obtained by image-capturing a plurality of target objects under predetermined observation conditions; and a display controller that highlights, in a display image related to a container having a plurality of storages respectively storing the plurality of target objects, storages of the container that belong to a group meeting a classification criterion selected by a user.

20 Claims, 38 Drawing Sheets

(51) Int. Cl.
  *G06V 20/10* (2022.01)
  *G06V 20/69* (2022.01)
(58) Field of Classification Search
  CPC ...... G02B 21/367; G02B 21/26; G02B 21/34; G02B 21/30; G06V 20/10; G06V 20/69; G06V 10/62; G06V 10/945; G06V 10/987; C12M 41/36; C12M 41/48; G06F 3/048; G06F 3/14
  See application file for complete search history.

(56) References Cited

U.S. PATENT DOCUMENTS

| | | | |
|---|---|---|---|
| 2010/0208960 A1* | 8/2010 | Kiyota | C12M 41/48 382/128 |
| 2014/0320513 A1* | 10/2014 | Ogi | G06V 20/695 345/581 |
| 2017/0199171 A1 | 7/2017 | Kiyota et al. | |
| 2019/0180080 A1* | 6/2019 | Iga | G01N 15/1429 |
| 2020/0240975 A1 | 7/2020 | Kiyota et al. | |
| 2020/0372652 A1 | 11/2020 | Hatto et al. | |
| 2021/0319345 A1* | 10/2021 | Kumar | G06F 16/285 |

FOREIGN PATENT DOCUMENTS

| | | |
|---|---|---|
| WO | 2015/193951 A1 | 12/2015 |
| WO | 2018/062125 A1 | 4/2018 |
| WO | 2019/159326 A1 | 8/2019 |

OTHER PUBLICATIONS

May 16, 2023 Extended Search Report issued in European Patent Application No. 19946930.5.

Jan. 7, 2020 International Search Report issued in International Patent Application No. PCT/JP2019/038163.

Mar. 15, 2022 International Preliminary Report on Patentability issued in International Patent Application No. PCT/JP2019/038163.

Aug. 2, 2024 Office Action issued in European Patent Application No. 19946930.5.

* cited by examiner

| EXPERIMENT NUMBER | EXPERIMENT NAME | EXPERIMENT SUPERVISOR | EXPERIMENT CONDUCTOR | OBSERVATION START DATE AND TIME | OBSERVATION END DATE AND TIME | MICROSCOPE NAME |
|---|---|---|---|---|---|---|
| Exp00001 | BS-T00001 | SUPERVISOR A | CONDUCTOR E | 2019/08/25 09:00:00 | 2019/08/26 15:15:25 | MICROSCOPE H |
| Exp00002 | BS-T00002 | SUPERVISOR B | CONDUCTOR F | 2019/08/30 14:30:00 | 2019/09/02 10:11:07 | MICROSCOPE H |
| Exp00003 | BS-T00003 | SUPERVISOR C | CONDUCTOR G | 2019/09/03 20:15:32 | 2019/09/03 20:15:32 | MICROSCOPE I |
| ... | ... | ... | ... | ... | ... | ... |

| MAGNIFICATION | CONTAINER PRODUCT | CONTAINER TYPE | ASSESSMENT RESULT | STATUS | APPLICATION NUMBER | APPLICATION NAME |
|---|---|---|---|---|---|---|
| 8x | PRODUCT TYPE K | 6WP | OK | COMPLETED | App.00001 | AppX |
| 8x | PRODUCT TYPE L | 6WP | NG | COMPLETED | App.00001 | AppX |
| 8x | PRODUCT TYPE K | 96WP |  | 60% | App.00002 | AppY |
| ... | ... | ... | ... | ... | ... | ... |

FIG. 7

EXPERIMENT LIST/ANALYSIS RESULTS/Well A-1

EXPERIMENT SEARCH

| | SPECIFY EXPERIMENT CONDUCTOR ∨ | STATUS ∨ | OBSERVATION START DATE ~ OBSERVATION END DATE | APPLICATION NAME ∨ | SEARCH |

EXPERIMENT LIST  < 1 ... 3 ... 125 >

| EXPERIMENT NAME | EXPERIMENT SUPERVISOR | EXPERIMENT CONDUCTOR | OBSERVATION START | OBSERVATION END | MICROSCOPE NAME | MAGNIFICATION | CONTAINER PRODUCT | CONTAINER TYPE | APPLICATION NAME | ASSESSMENT | STATUS | | |
|---|---|---|---|---|---|---|---|---|---|---|---|---|---|
| BS-T00001 | SUPERVISOR A | CONDUCTOR E | 2019/08/25 | 2019/08/26 | MICROSCOPE H | 8x | PRODUCT TYPE K | 6WP | App. 00001 | OK | COMPLETED | 🖉 | x |
| BS-T00002 | SUPERVISOR B | CONDUCTOR F | 2019/08/30 | 2019/09/02 | MICROSCOPE H | 8x | PRODUCT TYPE L | 6WP | App. 00001 | NG | COMPLETED | 🖉 | x |
| BS-T00003 | SUPERVISOR C | CONDUCTOR G | 2019/09/03 | | MICROSCOPE I | 8x | PRODUCT TYPE K | 96WP | App. 00002 | | 60% | 🖉 | x |
| BS-T00006 | SUPERVISOR B | CONDUCTOR J | 2019/08/01 | 2019/08/01 | MICROSCOPE K | 8x | PRODUCT TYPE K | 6WP | App. 00003 | OK | COMPLETED | 🖉 | x |
| BS-T00008 | SUPERVISOR D | CONDUCTOR J | 2018/12/24 | 2018/12/25 | MICROSCOPE K | 8x | PRODUCT TYPE M | 6WP | App. 00004 | OK | COMPLETED | 🖉 | x |
| BS-T00009 | SUPERVISOR A | CONDUCTOR E | 2019/02/04 | 2019/02/05 | MICROSCOPE K | 8x | PRODUCT TYPE M | 6WP | App. 00002 | NG | COMPLETED | 🖉 | x |
| BS-T00011 | SUPERVISOR A | CONDUCTOR E | 2019/05/13 | 2019/05/15 | MICROSCOPE H | 8x | PRODUCT TYPE N | 6WP | App. 00005 | NG | COMPLETED | 🖉 | x |
| BS-T00012 | SUPERVISOR F | CONDUCTOR H | 2018/11/11 | 2018/11/12 | MICROSCOPE H | 8x | PRODUCT TYPE K | 96WP | App. 00006 | NG | COMPLETED | 🖉 | x |

FIG. 21
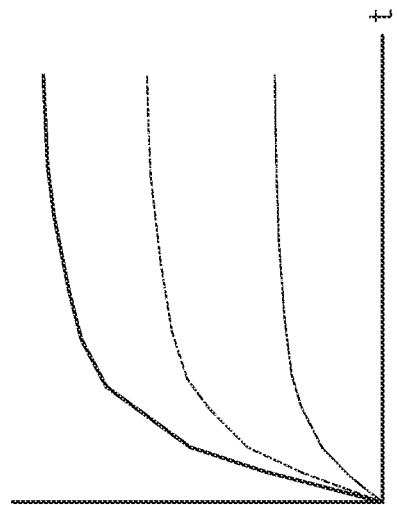
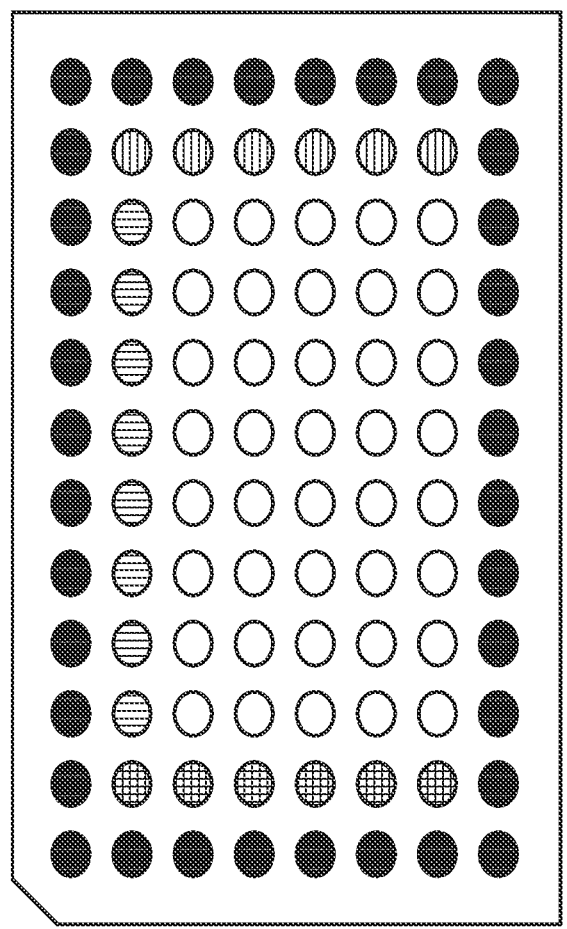

FIG. 29
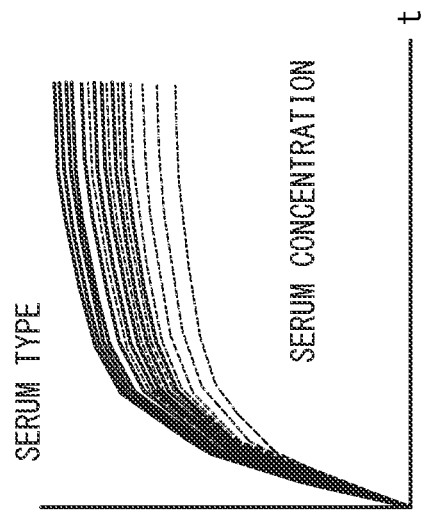
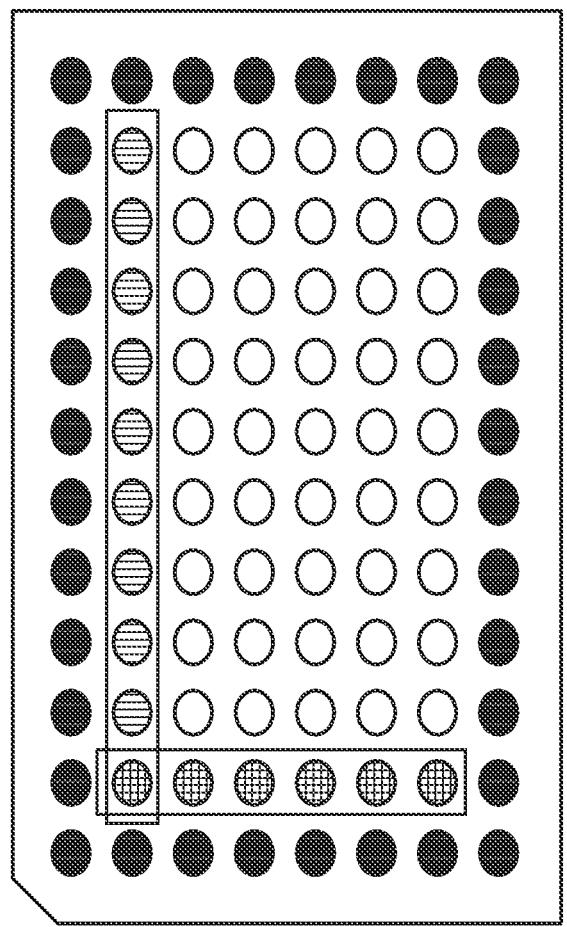
● ANTI-DRYING BUFFER FLUID
⊞ SERUM TYPE
⊟ SERUM CONCENTRATION FIG. 32
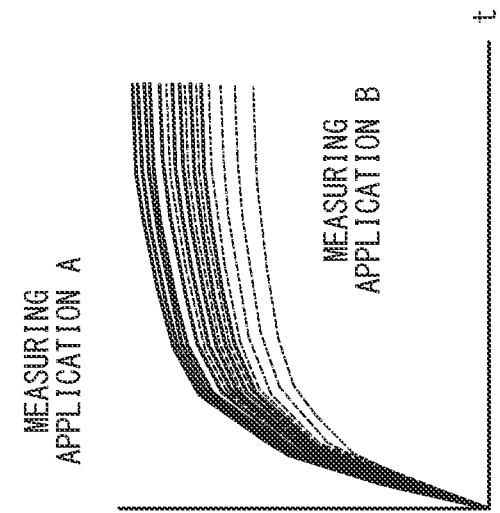
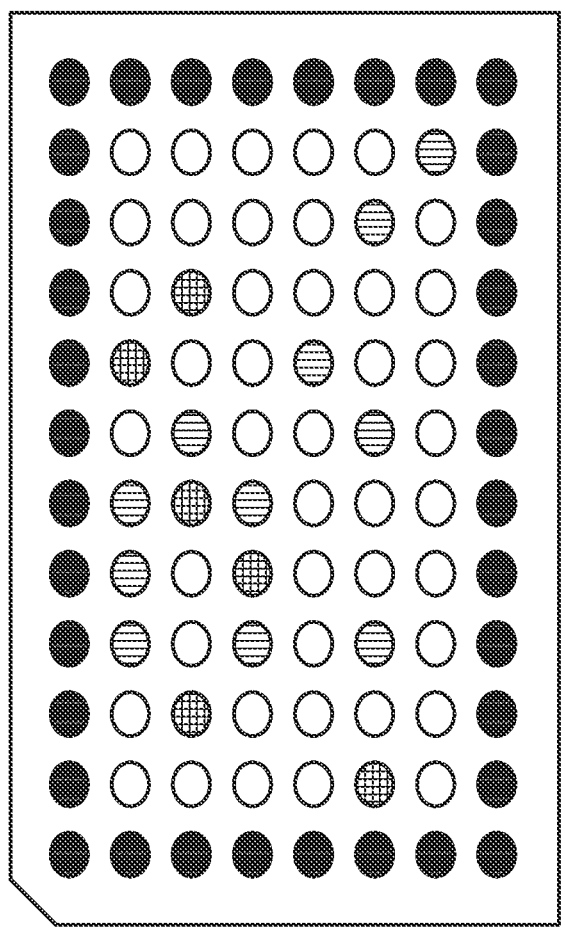
● ANTI-DRYING BUFFER FLUID
⊕ MEASURING APPLICATION A
⊖ MEASURING APPLICATION B

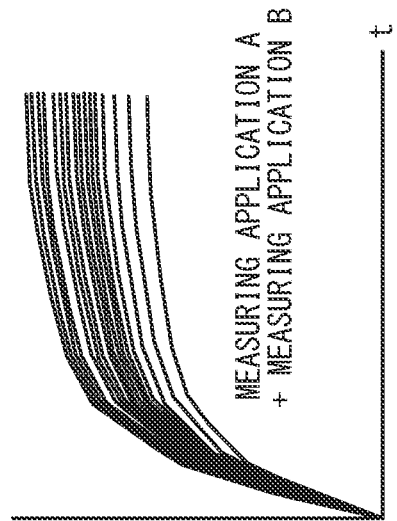
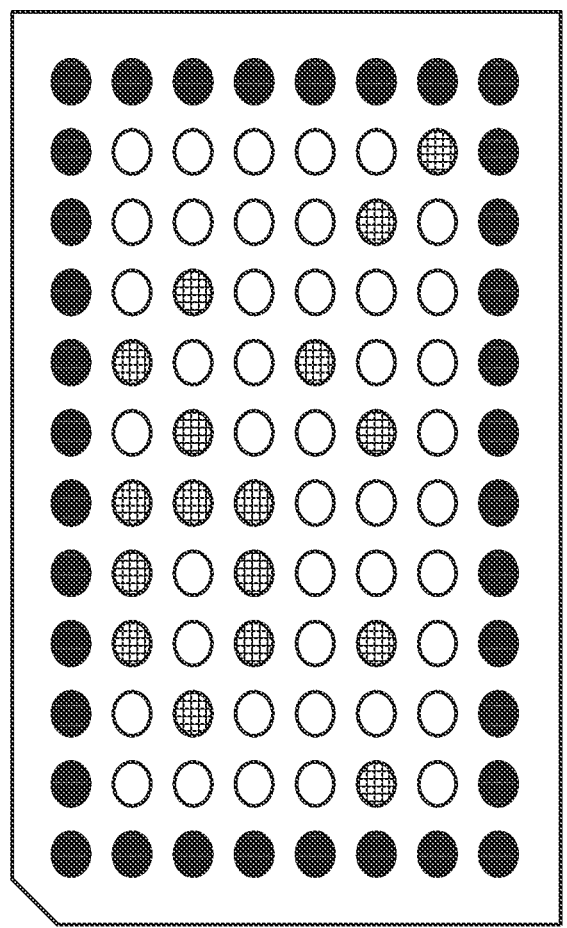
FIG. 36
● ANTI-DRYING BUFFER FLUID
○ MEASURING APPLICATION A
⊕ MEASURING APPLICATION A
  + MEASURING APPLICATION B

INFORMATION PROCESSING DEVICE, INFORMATION PROCESSING METHOD, INFORMATION PROCESSING PROGRAM, AND INFORMATION PROCESSING SYSTEM

TECHNICAL FIELD

The present invention relates to an information processing device, an information processing method, an information processing program, and an information processing system.

BACKGROUND ART

Patent Literature 1 discloses a technique for calculating, on the basis of an image of a colony of cells, a cell density from the area of the colony and the number of the cells contained in the colony of which the area has been calculated. For example, an analysis using such a technique yields a vast amount of results through day-to-day analytical work, and there is therefore a demand for a technique that enables a user to easily perform visual confirmation on those analytical results.

CITATION LIST

Patent Literature

[Patent Literature 1] International Publication No. 2015/193951

SUMMARY OF INVENTION

A first aspect of the invention is to provide an information processing device comprising: an acquirer that acquires observation results obtained by image-capturing a plurality of target objects under predetermined observation conditions; and a display controller that highlights, in a display image related to a container having a plurality of storages respectively storing the plurality of target objects, storages of the container that belong to a group meeting a classification criterion selected by a user.

A second aspect of the invention is to provide an information processing method comprising: acquiring observation results obtained by image-capturing a plurality of target objects under predetermined observation conditions; and highlighting, in a display image related to a container having a plurality of storages respectively storing the plurality of target objects, storages of the container that belong to a group meeting a classification criterion selected by a user.

A third aspect of the invention is to provide an information processing program that causes a computer to execute processes of: acquiring observation results obtained by image-capturing a plurality of target objects under predetermined observation conditions; and highlighting, in a display image related to a container having a plurality of storages respectively storing the plurality of target objects, storages of the container that belong to a group meeting a classification criterion selected by a user.

A fourth aspect of the invention is to provide an information processing system that outputs a display image to a user terminal by cloud computing, the information processing system comprising a server, wherein the server includes an acquirer that acquires observation results obtained by image-capturing a plurality of target objects under predetermined observation conditions, an image generator that highlights, in a display image related to a container having a plurality of storages respectively storing the plurality of target objects, storages of the container that belong to a group meeting a classification criterion selected by a user of the user terminal, and an outputter that outputs the display image generated by the image generator to the user terminal via a network.

A fifth aspect of the invention is to provide an information processing device comprising: an acquirer that acquires observation results obtained by image-capturing a plurality of target objects stored in a container having a plurality of storages under predetermined observation conditions; and a registerer that registers two or more of the storages as the same group, based on the observation results and a classification criterion obtained from the observation conditions or the observation results.

A sixth aspect of the invention is to provide an information processing method comprising: acquiring observation results obtained by image-capturing a plurality of target objects stored in a container having a plurality of storages under predetermined observation conditions; and registering two or more of the storages as the same group, based on the observation results and a classification criterion obtained from the observation conditions or the observation results.

A seventh aspect of the invention is to provide an information processing program that causes a computer to execute processes of: acquiring observation results obtained by image-capturing a plurality of target objects stored in a container having a plurality of storages under predetermined observation conditions; and registering two or more of the storages as the same group, based on the observation results and a classification criterion obtained from the observation conditions or the observation results.

An eighth aspect of the invention is to provide an information processing system that executes processing by cloud computing, the information processing system comprising a server, wherein the server includes an acquirer that acquires observation results obtained by image-capturing a plurality of target objects stored in a container having a plurality of storages under predetermined observation conditions, and a registerer that registers two or more of the storages as the same group, based on the observation results and a classification criterion obtained from the observation conditions or the observation results.

The summary clause does not necessarily describe all necessary features of the embodiments of the present invention. The present invention may also be a sub-combination of the features described above.

BRIEF DESCRIPTION OF THE DRAWINGS

FIG. 6 is a diagram showing an example of information stored in a memory storage device according to a first embodiment.

FIG. 7 is a diagram showing a screen example in group registration according to the first embodiment.

FIG. 9 is a diagram showing a screen example in the group registration according to the first embodiment.

FIG. 10 is a diagram showing a screen example in the group registration according to the first embodiment.

FIG. 11 is a diagram showing a screen example in the group registration according to the first embodiment.

FIG. 12 is a diagram showing a screen example in the group registration according to the first embodiment.

FIG. 13 is a diagram showing a screen example in the group registration according to the first embodiment.

FIG. 14 is a diagram showing a screen example in the group registration according to the first embodiment.

FIG. 15 is a diagram showing a screen example in the group registration according to the first embodiment.

FIG. 16 is a diagram showing a screen example in the group registration according to the first embodiment.

FIG. 17 is a diagram showing a screen example in the group registration according to the first embodiment.

FIG. 21 is a diagram showing an example of a plate map according to the second embodiment.

FIG. 29 is a diagram showing an example of a plate map according to the third embodiment.

FIG. 32 is a diagram showing an example of a plate map according to the fourth embodiment.

FIG. 36 is a diagram showing an example of a plate map according to the fifth embodiment.

DESCRIPTION OF EMBODIMENTS

Figure 1:
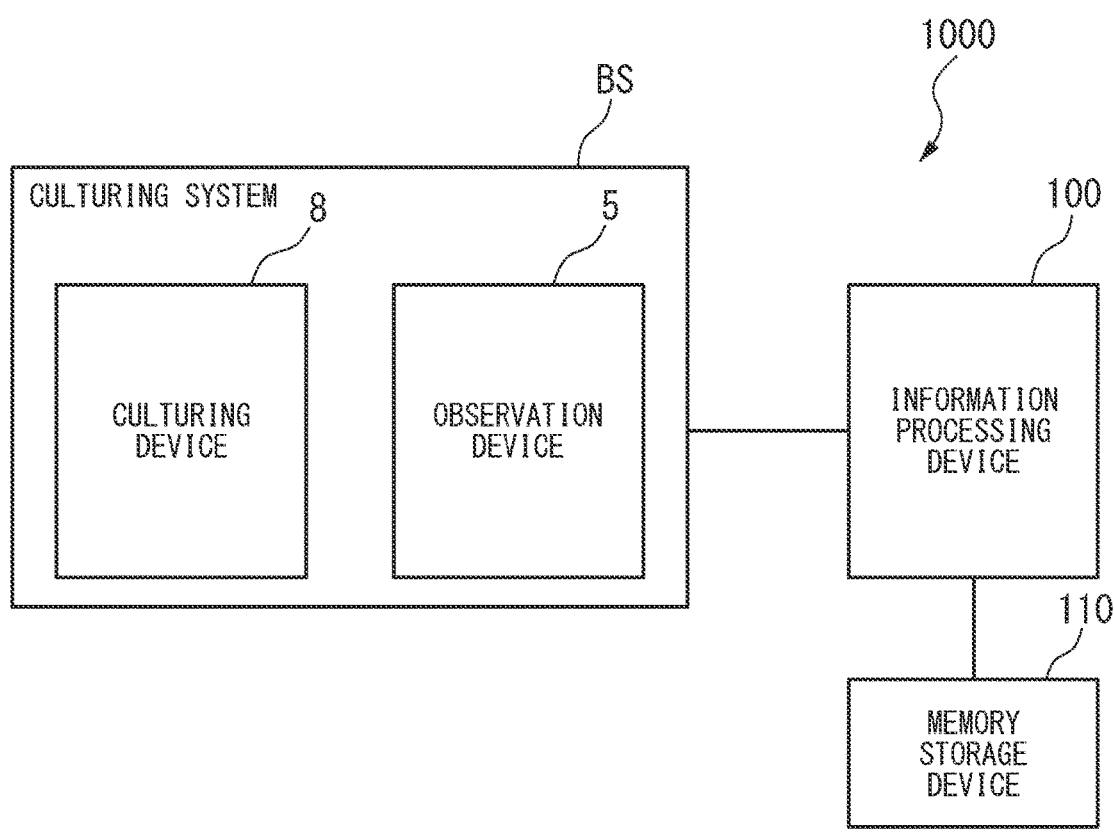
FIG. 1 is a diagram showing an overall configuration example of an analysis system including an information processing device according to a first embodiment.

Hereunder, embodiments of the present invention will be described, with reference to the drawings. It should be noted that, in the drawings, scale is changed as necessary to illustrate the embodiments, such as by enlarging or by emphasizing a part, and thus, the embodiments may differ from the actual product in size and shape in some cases.

First Embodiment

Hereunder, a first embodiment will be described. FIG. 1 is a diagram showing an overall configuration example of an analysis system including an information processing device according to the first embodiment. As shown in FIG. 1, an analysis system 1000 includes a culturing system BS, an information processing device 100, and a memory storage device 110. The culturing system BS includes a culturing device 8 and an observation device 5. The analysis system 1000 is a system for culturing target objects (for example, cells, samples, or specimens), observing (image-capturing) the process of culturing, and analyzing observation results (for example, captured images).

The culturing system BS, the information processing device 100, and the memory storage device 110 are connected via a network such as the Internet, LAN (Local Area Network), or WAN (Wide Area Network). The culturing system BS, the information processing device 100, and the memory storage device 110 may also be connected via a network composed of a combination of the Internet, a LAN (Local Area Network), and a WAN (Wide Area Network). Such a network is not limited to a wired communication network, and may include a wireless communication network. The information processing device 100 may include the memory storage device 110. The culturing system BS and the memory storage device 110 may be connected via a network.

Figure 2:
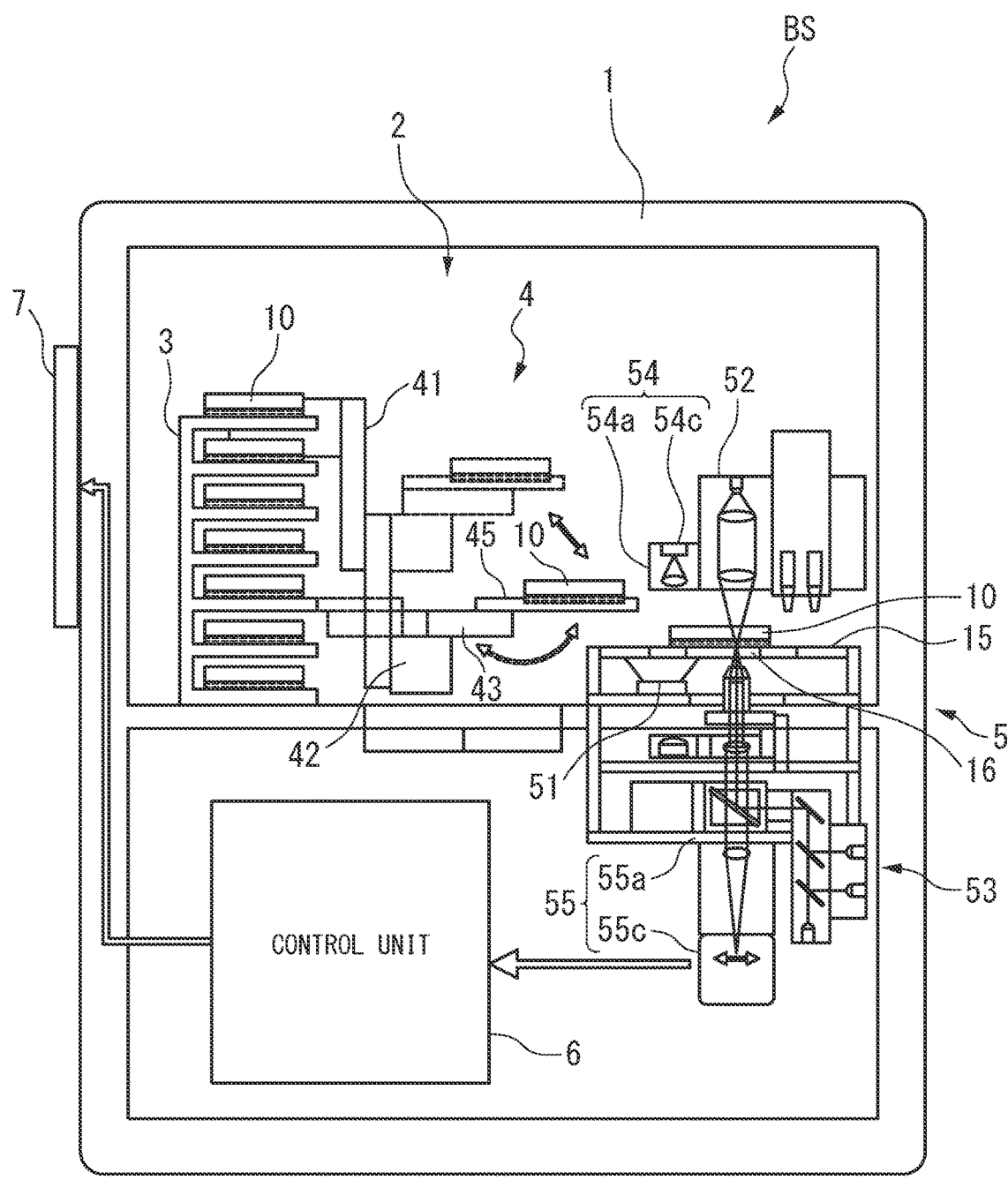
FIG. 2 is a diagram showing a configuration example of a culturing system connected to the information processing device according to the first embodiment.
Figure 3:
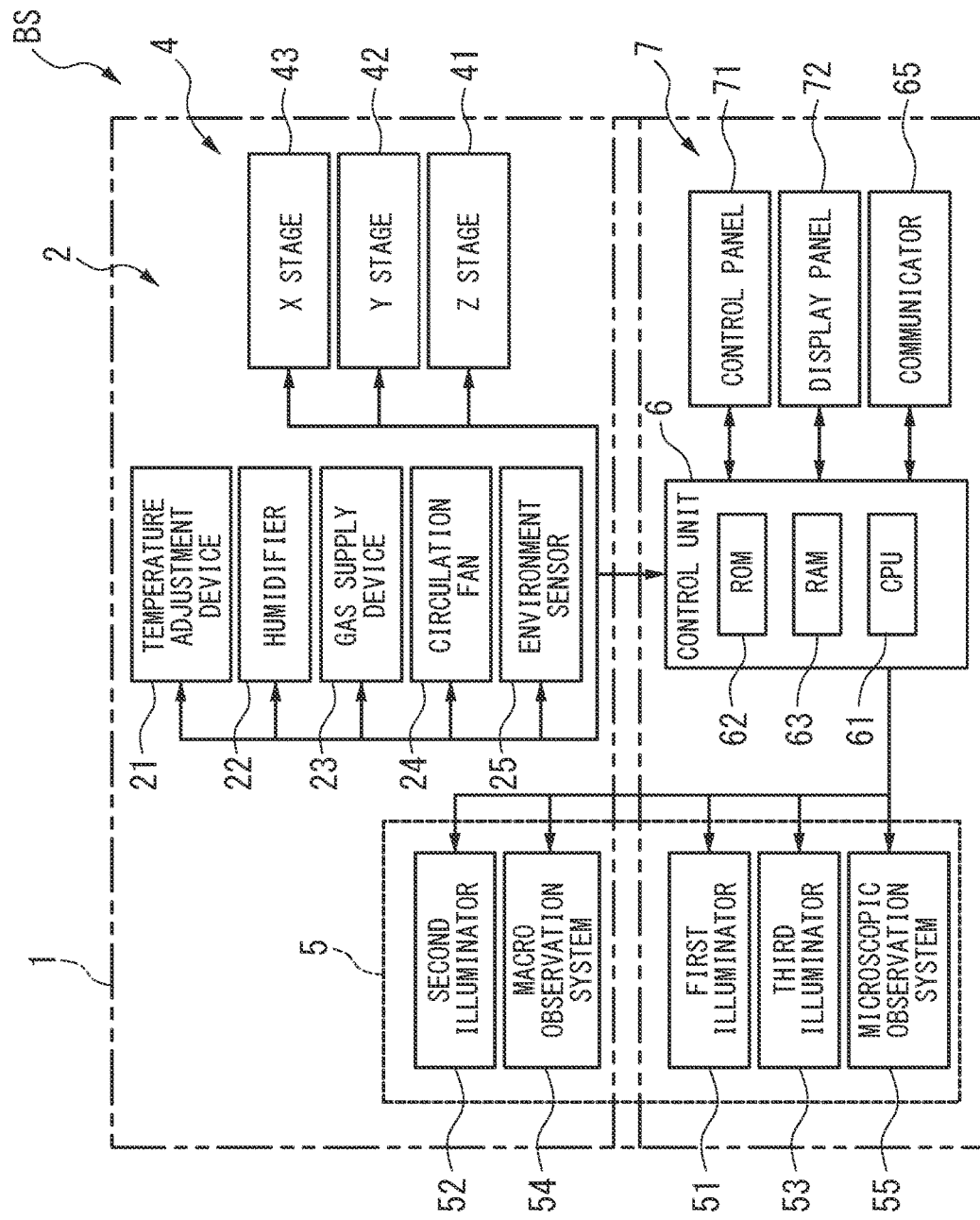
FIG. 3 is a block diagram showing a configuration example of the culturing system connected to the information processing device according to the first embodiment.
Figure 4:
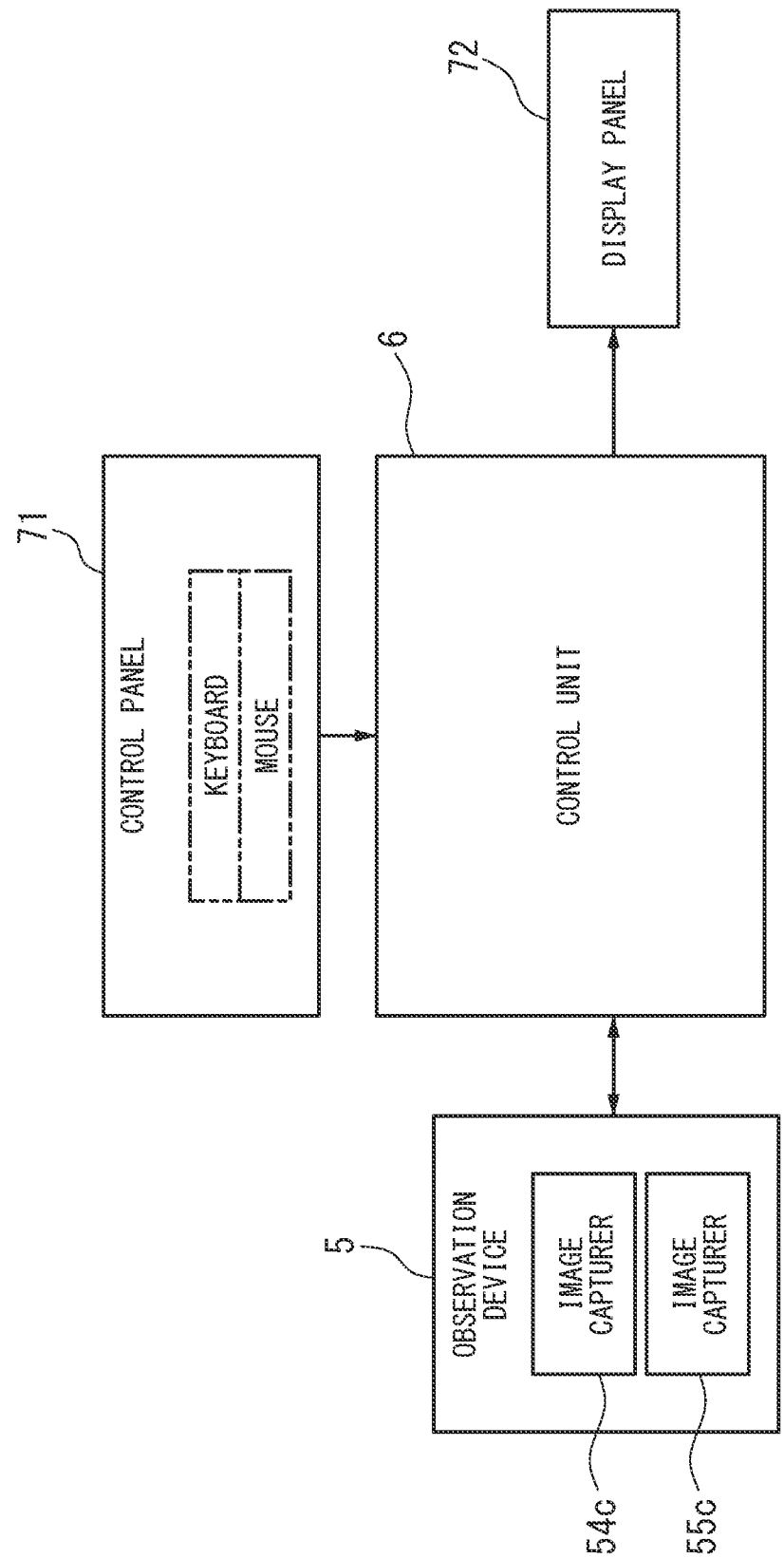
FIG. 4 is a diagram for describing an example of connections around a control unit of the culturing system connected to the information processing device according to the first embodiment.

FIG. 2 is a diagram showing a configuration example of the culturing system connected to the information processing device according to the first embodiment. FIG. 3 is a block diagram showing a configuration example of the culturing system connected to the information processing device according to the first embodiment. FIG. 4 is a diagram for describing an example of connections around a control unit of the culturing system connected to the information processing device according to the first embodiment.

Broadly speaking, the culturing system BS has a culturing chamber 2 provided in an upper part of a casing 1, a stocker 3 that stores and holds a plurality of culture vessels 10, an observation device 5 that observes (image-captures) target objects in the culture vessels 10, and a transport unit (transport device) 4 that transports the culture vessels 10. In addition, the culturing system BS has a control unit (control device) 6 that controls the operation of the system, and an operation panel 7 including a display device. The culturing chamber 2, the stocker 3, the transport unit 4, and so forth correspond to the culturing device 8.

The culturing chamber 2 is a chamber that forms a culturing environment in microscopic observation for observation objects such as cells. In the culturing chamber 2 there are provided a temperature adjustment device 21, a humidifier 22, a gas supply device 23, a circulation fan 24, and an environment sensor 25. The temperature adjustment device 21, in coordination with the environment sensor 25, adjusts the temperature within the culturing chamber 2 to a predetermined set temperature. The humidifier 22, in coordination with the environment sensor 25, adjusts the humidity within the culturing chamber 2 to a predetermined set humidity. The gas supply device 23 supplies $CO_2$ gas, $N_2$ gas, $O_2$ gas, or the like, in coordination with the environment sensor 25. The circulation fan 24 is a fan that, in coordination with the environment sensor 25, circulates the gas (air) within the culturing chamber 2 to thereby adjust the temperature. The environment sensor 25 detects the temperature, the humidity, the carbon dioxide concentration, nitrogen concentration, oxygen concentration, or the like within the culturing chamber 2.

The stocker 3 is formed in the shape of a rack that is sectioned along the front-rear direction as well as along the upper-lower direction. Each rack shelf has, for example, a unique address set therefor. Culture vessels 10 are appropriately selected according to the type and purpose of the target object to be cultured. The culture vessels 10 may be, for example, well plates, flasks, or dish type culture vessels. In the present embodiment, well plates are used as an example. Target objects are injected into the culture vessel 10 together with a liquid medium (culture fluid) and held thereon. For example, a code number is assigned to each of the culture vessels 10. Each culture vessel 10 is stored in the stocker 3 in association with the specified address thereof, according to the code number assigned thereto. The transport unit 4 has a Z stage 41 that can move up and down, a Y stage 42 that can move forward and backward, and an X stage 43 that can move left and right, which are provided inside the culturing chamber 2. A supporting arm 45 lifts and supports the culture vessel 10 on the distal end side of the X stage 43.

The observation device 5 has a first illuminator 51, a second illuminator 52, a third illuminator 53, a macro observation system 54, a microscopic observation system 55, and a control unit 6. The first illuminator 51 illuminates a target object from below a sample stage 15. The second illuminator 52 illuminates a target object from above the sample stage 15, along the optical axis of the microscopic observation system 55. The third illuminator 53 illuminates a target object from below the sample stage 15, along the optical axis of the microscopic observation system 55. The macro observation system 54 performs macro observation of a target object. The microscopic observation system 55 performs micro observation of a target object. In the sample stage 15, a transparent window 16 composed of a material such as glass is provided within an observation region of the microscopic observation system 55.

The macro observation system 54 has an observation optical system 54a and an image capturer 54c such as a CCD camera that captures an image of a target object formed by the observation optical system 54a. The macro observation system 54 acquires an overall observation image from above the culture vessel 10 backlit by the first illuminator 51. The microscopic observation system 55 has an observation optical system 55a including an objective lens, an intermediate variable magnification lens, and a fluorescence filter, and an image capturer 55c such as a cooled CCD camera that captures an image of a target object formed by the observation optical system 55a. A plurality of the objective lenses and a plurality of the intermediate variable magnification lenses may respectively be provided. The objective lens and the intermediate variable magnification lens can be set for any observation magnification by changing the combination of lenses. The microscopic observation system 55 acquires a transmitted image of a target object illuminated by the second illuminator 52, a reflected image of the target object illuminated by the third illuminator 53, and a fluorescence image of the target object illuminated by the third illuminator 53. That is to say, the microscopic observation system 55 acquires a microscopic observation image obtained by microscopically observing a target object in the culture vessel 10.

The control unit 6 processes signals input from the image capturer 54c of the macro observation system 54 and the image capturer 55c of the microscopic observation system 55, and generates images such as an overall observation image and a microscopic observation image. The control unit 6 performs image analysis on overall observation images and microscopic observation images to generate a time-lapse image. The control unit 6 outputs the generated image to the information processing device 100 and stores it in the memory storage device 110.

The control unit 6 has a CPU (Central Processing Unit) (processor) 61, a ROM (Read-Only Memory) 62, and a RAM (Random Access Memory) 63. The CPU 61 performs overall control of the control unit 6 and executes various processes in the control unit 6. The ROM 62 stores a control program and control data related to the culturing system BS. The RAM 63 includes an auxiliary memory storage device such as a hard disk or a DVD (Digital Versatile Disc), and temporarily stores observation conditions, image data, and so forth. Each of the units such as the culturing chamber 2, the transport unit 4, the observation device 5, and the operation panel 7 is connected to the control unit 6 (see FIG. 3).

The RAM 63 stores, for example, environmental conditions of the culturing chamber 2 according to an observation program, an observation schedule, an observation type, an observation position, an observation magnification, and so forth in the observation device 5. The RAM 63 includes a memory region for storing image data captured by the observation device 5, and stores the image data in association with index data including the code number of the culture vessel 10, the date and time of image capturing, and so forth. The operation panel 7 has an operational panel (operator, inputter) 71 and a display panel 72. The operational panel 71 includes input/output devices (operator, inputter) such as a keyboard, a mouse, and a switch. The user operates the operational panel 71 to input observation program settings, condition selections, operation instructions, and so forth. The communicator 65 is compliant with wired and wireless communication standards, and transmits and receives data to and from the observation device 5, the culturing system BS, or external devices (for example, a server, user's client terminal) connected to the control unit 6. Various types of information stored in the RAM 63 can be appropriately stored in the memory storage device 110 via the information processing device 100.

Figure 5:
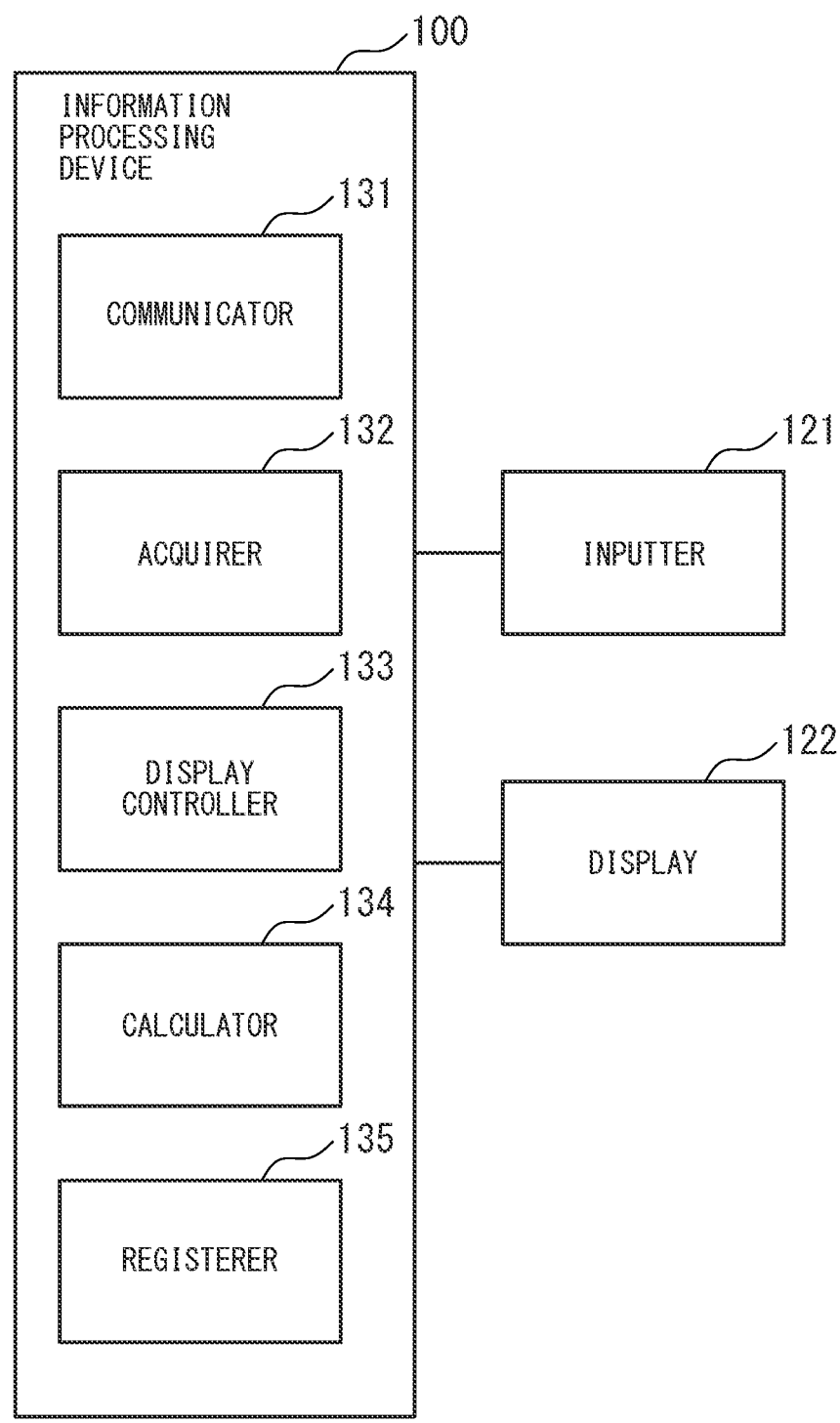
FIG. 5 is a block diagram showing a functional configuration example of the information processing device according to the first embodiment.

FIG. 5 is a block diagram showing a functional configuration example of the information processing device according to the first embodiment. As shown in FIG. 5, the information processing device 100 has a communicator 131, an acquirer 132, a display controller 133, a calculator 134, and a registerer 135. An inputter 121 and a display 122 are connected to the information processing device 100.

The inputter 121 accepts various operations performed by the user of the information processing device 100 and outputs a control signal according to the user operation. The inputter 121 includes, for example, a mouse and a keyboard. The display 122 outputs display of various information (information including images) according to the user operation performed on the inputter 121. The display 122 includes, for example, a display or the like. The inputter 121 and the display 122 may be integrally configured. That is to say, the inputter 121 and the display 122 may be configured as a portable terminal (for example, a tablet terminal) having a touch panel, on which direct input operations are performed for various information displayed on the display 122.

The communicator 131 communicates with the culturing system BS and the memory storage device 110 via a network and transmits and receives various information thereto and therefrom. The communicator 131, for example, receives information related to observation conditions and observation results from the culturing system BS. The communicator 131, for example, transmits and receives information related to observation conditions and observation results to and from the memory storage device 110.

The acquirer 132 acquires observation results obtained by image-capturing a plurality of target objects stored in a container having a plurality of storages under predetermined observation conditions. For example, the acquirer 132 appropriately acquires information related to the results of various observations in the culturing system BS stored in the memory storage device 110, from the memory storage device 110 via the network or the communicator 131. The acquirer 132 can appropriately acquire not only information related to observation results but also information related the observation conditions from the memory storage device 110.

FIG. 6 is a diagram showing an example of information stored in the memory storage device according to the first embodiment. As shown in FIG. 6, the memory storage device 110 includes, as data items, experiment number, experiment name, experiment supervisor, experiment conductor, observation start date and time, observation end date and time, microscope name, magnification, container product, container type, assessment result, status, application number, and application name. The experiment number is information indicating an identification number uniquely assigned to each experiment. For example, the experiment number stores information such as "Exp00001". The experiment name is information indicating the name of an experiment. For example, the experiment name stores information such as "BS-T00001". The experiment supervisor is information indicating the name of a person responsible for an experiment. For example, the experiment supervisor stores information such as "Supervisor A". The experiment conductor is information indicating the name of a person that conducts an experiment. For example, the experiment conductor stores information such as "Conductor E". The data items such as the experiment number, the experiment name, the experiment supervisor, and the experiment conductor may respectively be simply data items such as number, name, supervisor, and conductor. For example, when used not only in an experimental process but also in a culturing process, these data items may be data items such as culturing number, culturing name, culturing supervisor, and culturing conductor.

The observation start date and time is information indicating the date and time on and at which an observation started. For example, the observation start date and time stores information such as "2019/08/25 09:00:00". The observation end date and time is information indicating the date and time on and at which an observation ended. For example, the observation end date and time stores information such as "2019/08/26 15:15:25". The microscope name is information indicating the name of a microscope used for observation. For example, the experiment name stores information such as "Microscope H". The magnification is information indicating the magnification of a microscope set at the time of observation. For example, the magnification stores information such as "8×". The container product is information indicating the manufacturer name of a container (for example, a well plate or the like) having a plurality of storages (for example, wells, dishes, or the like) for storing target objects. For example, the container product stores information such as "Product type K".

The container type is information indicating the type of a container (for example, a well plate or the like) having a plurality of storages (for example, wells, dishes, or the like) for storing target objects. For example, the container type stores information such as "6WP (Well Plate)". The assessment result is information indicating user's assessment of an experiment. For example, the assessment result stores information such as "OK" or "NG". The status is information indicating the analytical progress of an observation result. For example, the status stores information such as "Completed" or "60%". The application number is information indicating an identification number uniquely assigned to each application package used for an observation result analysis. For example, the application number stores information such as "App.00001". The application name is information indicating the name of an application package. For example, the application name stores information such as "AppX". Examples of an application package include an application for analyzing images, an application for calculating the area of a target object, an application for calculating the number of target objects.

In addition to the information mentioned above, the memory storage device 110 stores an observation image of a plurality of storages, in which target objects are stored respectively, in association with an experiment number, a code number, and so forth. An observation image corresponds to, for example, the overall observation image or microscopic observation image mentioned above. Therefore, the acquirer 132 can also appropriately acquire an observation image from the memory storage device 110. The memory storage device 110 also stores group information described later.

Now, let us return to the description of FIG. 5. The display controller 133 generates a display image to be displayed on the display 122, and displays the generated display image on the display 122. The display controller 133 generates various display images to be displayed on the display 122 and displays the generated display images on the display 122, however, in the present embodiment, the display controller 133 primarily generates a display image related to group registration executed by the registerer 135 described later. The display controller 133 acquires from the calculator 134 information that requires calculation in relation to generation of a display image. That is to say, the calculator 134 executes calculation based on observation results. In other words, the display controller 133 acquires raw data such as observation conditions and observation results from the memory storage device 110, and acquires from the calculation unit 134 information on calculation processing results based on the observation results. The processing performed by the display controller 133 according to the present embodiment will be described in detail later.

The registerer 135 registers two or more of the storages as the same group, based on the observation results and a classification criterion obtained from the observation conditions or the observation results. For example, a classification criterion is at least one of the observation conditions including the type and amount of a culture fluid to be charged into the storage. For example, a classification criterion is at least one of the observation conditions including the type, concentration, and amount of a serum included in a culture fluid to be charged into the storage. For example, a classification criterion is at least one of the observation conditions including the type, concentration, exposure duration, and exposure timing of a medicament to be charged into the storage. For example, a classification criterion is at least one of the observation conditions including the type and number of target objects to be charged into the storage. For example, a classification criterion is at least one of the observation conditions including the microscope name, the magnification, the temperature setting, humidity setting, atmosphere supply setting, and light output setting in the space in which the container is arranged (for example, culturing chamber 2). For example, a classification criterion is at least one of the observation results including the number of, temporal change in the number of, doubling time of the number of, movement amount of, and form changes in the target objects. For example, a classification criterion is at least one of the observation results including the area that covers target objects and the perimeter length of the target objects. As a classification criterion, for example, the luminance value after an observation result (image) analysis may be used. For example, in the case where using the luminance value after an image analysis, when the average luminance value is "5" with respect to the cell density (crude density) of a colony and the average value is taken as a reference value, values equal to or greater than the reference value and values less than the reference value can be used for classification. That is to say, the registerer 135 registers two or more storages having the same (similar or related) one or a combination of the above classification criteria and observation results, as the same group. The registerer 135 stores group information in the memory storage device 110. The classification criteria include, for example, a feature or index used for group registration and group display described later.

The information used for group registration may include an observation image of a storage, which is one of observation results. That is to say, the registerer 135 registers two or more storages having the same (similar or related) observation image during any stage (period) of an observation, as the same group. The information used for group registration may include information that visually represents observation results. That is to say, the registerer 135 registers two or more storages having the same (similar or related) information that is graphically represented information on the basis of the information graphically representing the observation result, as the same group.

Group registration can also be performed without using observation results. For example, the registerer 135 executes group registration at an arbitrary timing without using observation results. Examples of the arbitrary timing include before, during, and/or after an observation. As an example, group registration that does not use observation results can be performed before an observation (at a timing at which classification criteria related to observation conditions are set). That is to say, the registerer 135 may register two or more of the storages as the same group, based on classification criteria related to observation conditions. The classification criteria related observation conditions may be predetermined by the user.

FIG. 7 to FIG. 17 are diagrams each showing a screen example in a group registration that uses classification criteria according to the first embodiment. In the description of FIG. 7 to FIG. 17, the processes in the display controller 133, the calculator 134, and the registerer 135 will be described as appropriate. As shown in FIG. 7, the display controller 133 displays a display image showing an observation result search screen on the display 122. The observation result search screen includes a text input field KSa for performing keyword search, conditional search fields FSa, FSb, FSc, and FSd for performing a search by making a selection from predetermined search conditions, and a search button SB for executing a search. For example, the condition search field FSa is a pull-down menu for selecting the name of an experiment conductor. For example, the condition search field FSb is a pull-down menu for selecting a status. For example, the condition search field FSc has pull-down menus for selecting an observation start date and time and an observation end date and time. For example, the condition search field FSd is a pull-down menu for selecting an application name. The conditional search fields FSa, FSb, FSc, and FSd may be realized by text input fields. The search conditions are not limited to the above examples.

The user operates the inputter 121, inputs text to the text input field KSa, makes selections using the conditional search fields FSa, FSb, FSc, and FSd, and presses the search button SB. Alternatively, the user operates the inputter 121 and presses the search button SB without performing text input or making search condition selections. Upon pressing the search button SB, the display controller 133 acquires information corresponding to the search conditions from the memory storage device 110, and displays a display image showing a search result field SR on the display 122. That is to say, the display controller 133 displays on the display 122 a display image showing a list of observation results based on the search conditions or a list of all observation results. For example, the search result field SR includes information on data items such as experiment name, experiment supervisor, experiment conductor, observation start date and time, observation end date and time, microscope name, magnification, container product, container type, application name, assessment, and status. However, data items of the search result field SR are not limited to the above examples. Sorting can be performed in the search result field SR, using a data item instruction or the like. The user performs an operation of making a selection (specifying) from the search result field SR in order to confirm an observation result.

Figure 8:
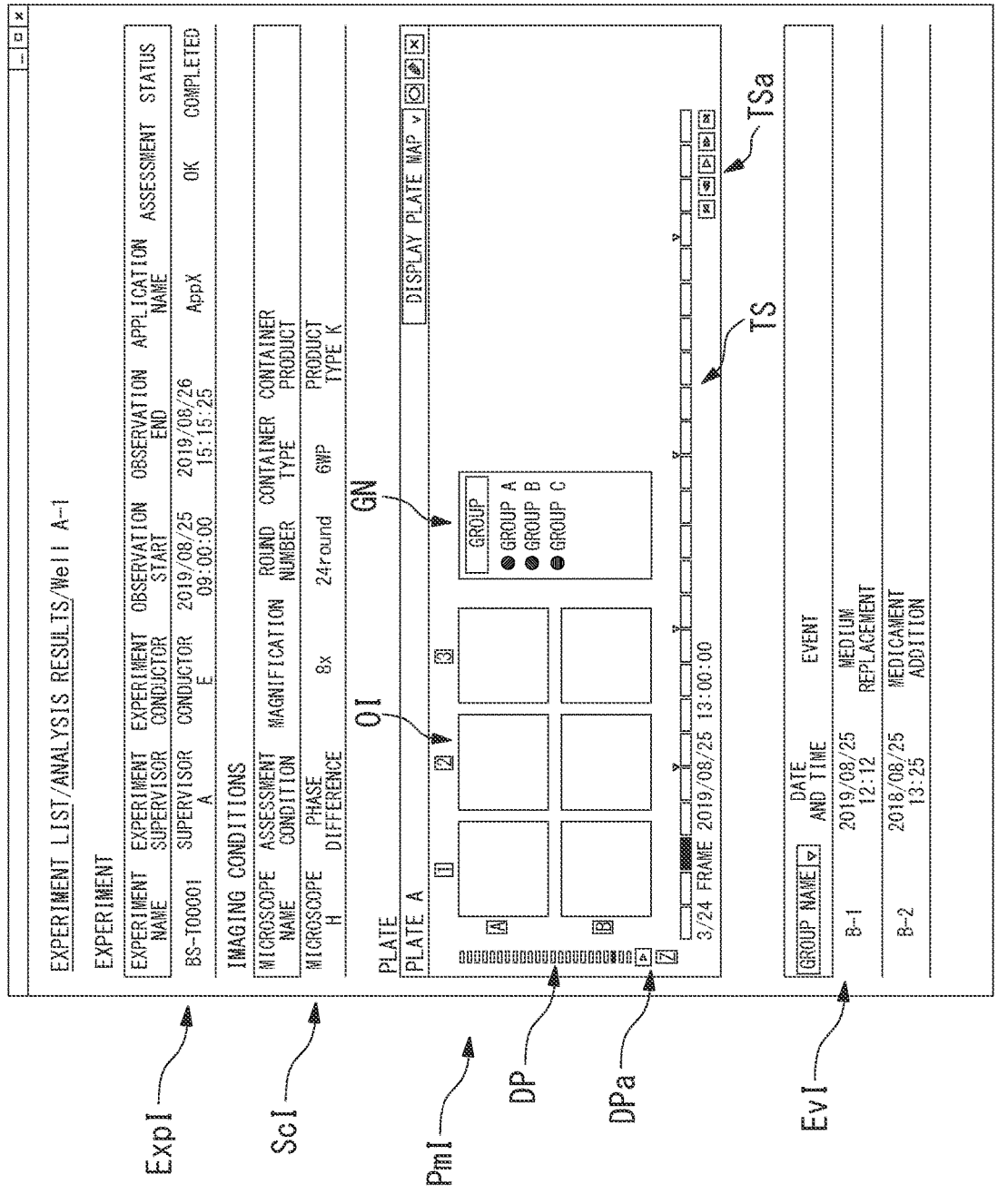
FIG. 8 is a diagram showing a screen example in the group registration according to the first embodiment.

Next, as shown in FIG. 8, the display controller 133 shows on a display image the observation result selected from the search result field SR. The display image of the observation result includes, for example, an information field ExpI related to observation, an information field ScI related to image capturing conditions (observation conditions), a plate map field PmI including observation images, and an information field EvI related to events in observations. Of these, the plate map field PmI includes observation image fields OI, a group name field GN, a time-series switching content field TS, and a depth switching content field DP. For example, each observation image field OI displays an observation image included in a selected observation result. For example, the group name field GN displays registered group names. For example, the time-series switching content field TS displays contents for switching observation images in time series manner. For example, the depth switching content field DP displays contents for switching observation images corresponding to the depths of storages.

The time-series switching content field TS is represented by, for example, a plurality of rectangles separated at regular intervals. The user can operate the inputter 121 to select a rectangle in the time-series switching content field TS. When a rectangle in the time-series switching content field TS is selected, the display controller 133 switches the display of the plate map field PmI using the observation image corresponding to the corresponding period as a display image. At this time, the display controller 133 may display information related the observation date and time of the selected rectangle. Switching of observation images using the time-series switching content field TS is not limited to selecting a rectangle, and may be realized by a time-series switching content field TSa that moves the position of the selected rectangle.

The depth switching content field DP is represented by, for example, rectangles separated at certain depths (thicknesses in the Z direction) with respect to the storage. The user can operate the inputter 121 to select a rectangle in the depth switching content field DP. When a rectangle in the depth switching content field DP is selected, the display controller 133 switches the display of the plate map field PmI using the observation image corresponding to the corresponding depth of the storage as a display image. Switching of observation images using the depth switching content DP is not limited to selecting a rectangle, and may be realized by a depth switching content field DPa that moves the position of the selected rectangle.

That is to say, the display controller 133 shows the observation results of the group selected by the user, on a display image related to a container having a plurality of storages, and displays the display image on the display 122. When no search condition is used, the display controller 133 shows observation results selected from a list (a list of all results) by the user, on a display image related to a container having a plurality of storages, and displays the display image on the display 122. When search conditions are used, the display controller 133 shows observation results selected by the user from a list based on the search conditions, on a display image related to a container having a plurality of storages, and displays the display image on the display 122. The display controller 133 shows the observation images of the storages included in the observation results, on the display image, and displays the display image on the display 122.

Figure 9:
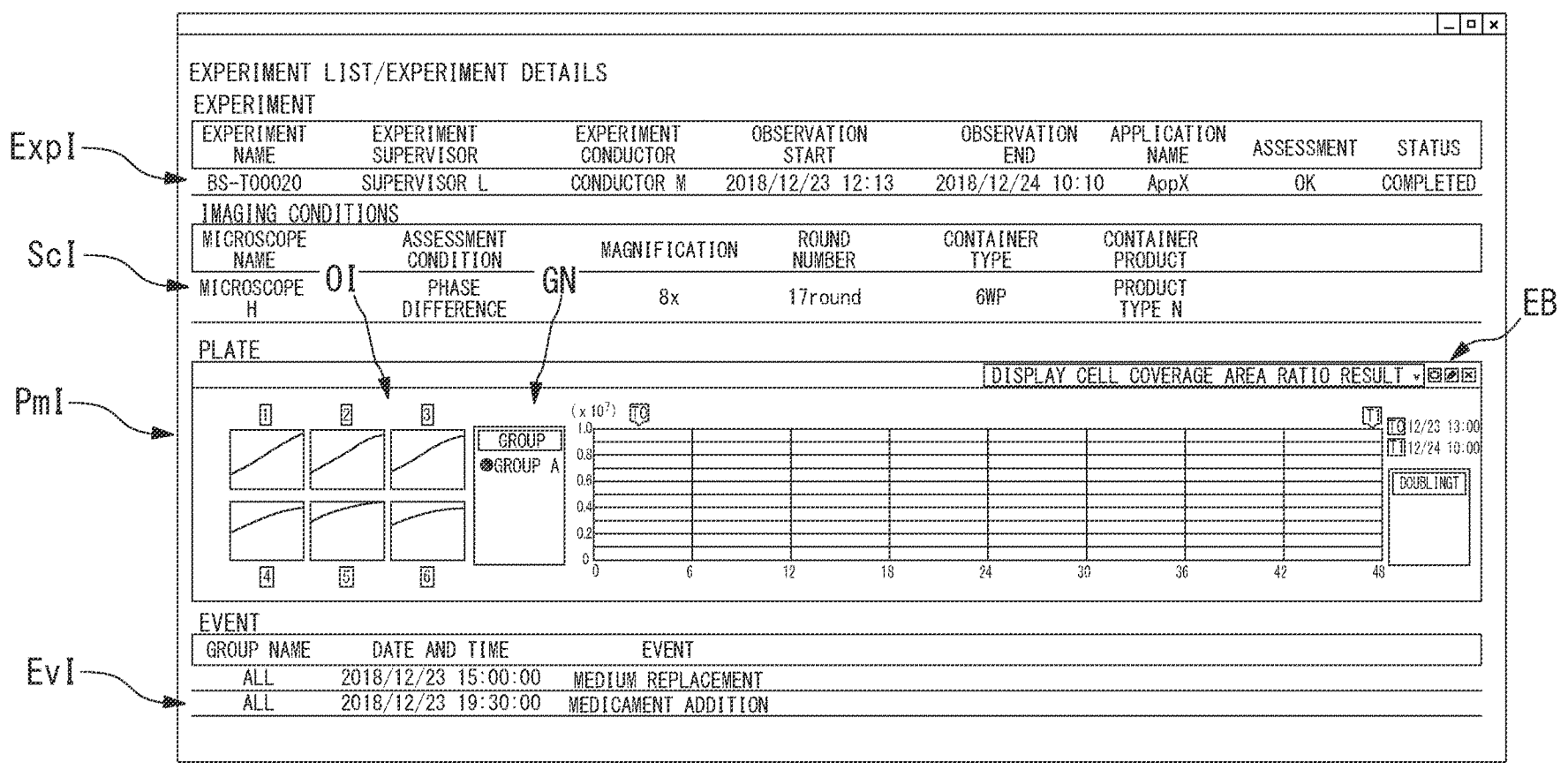
Figure 10:
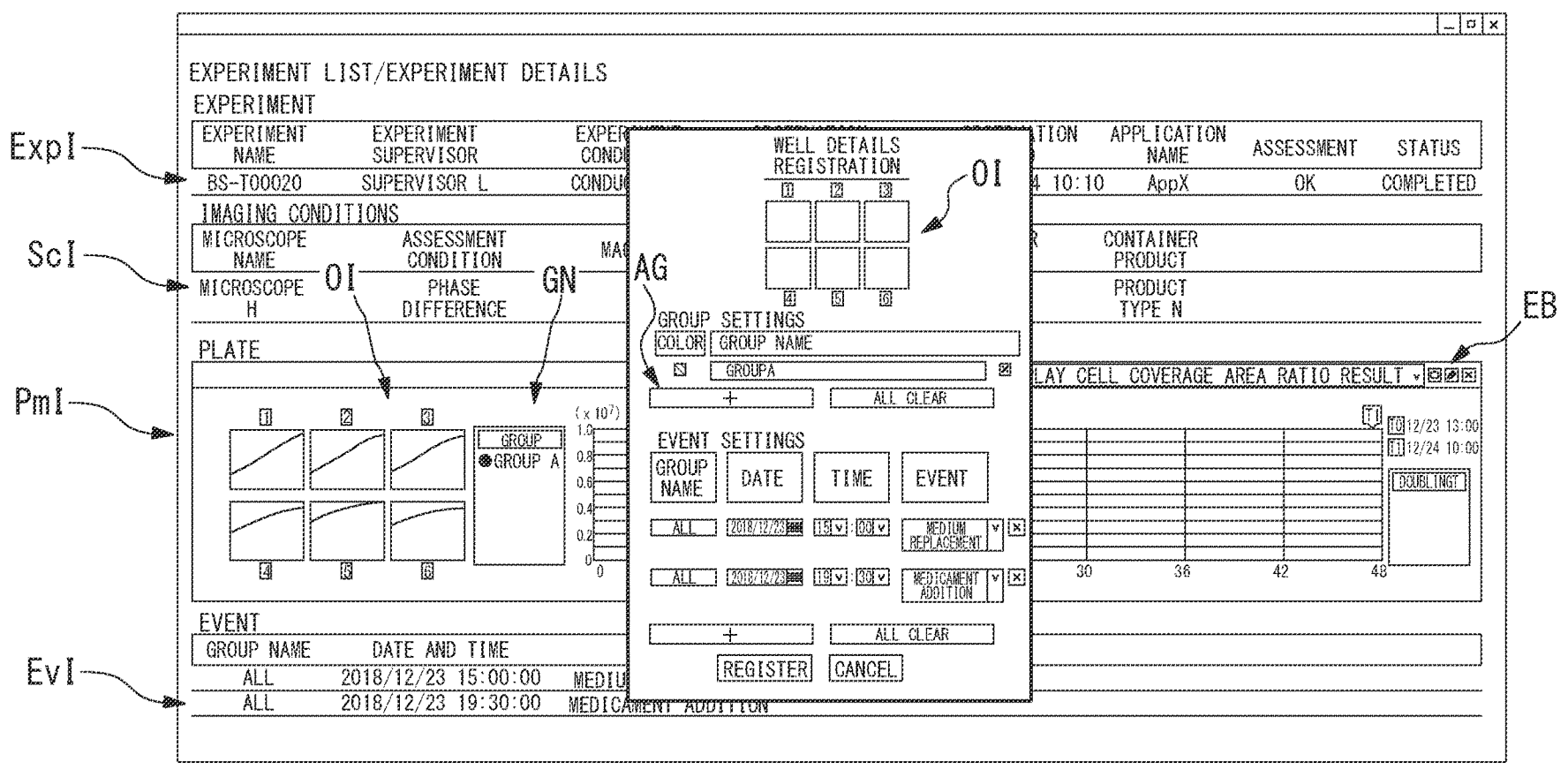
Figure 11:
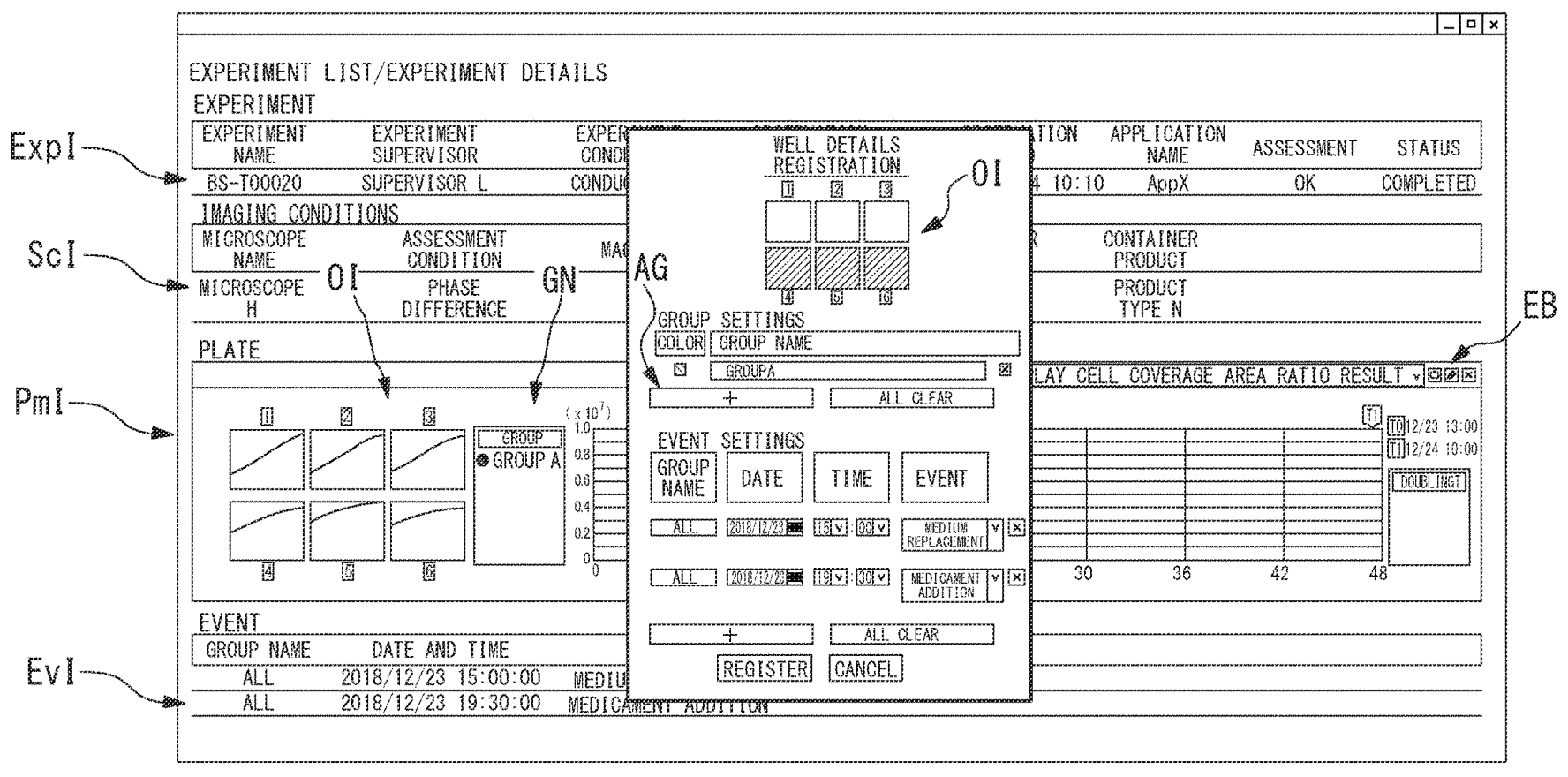
Figure 12:
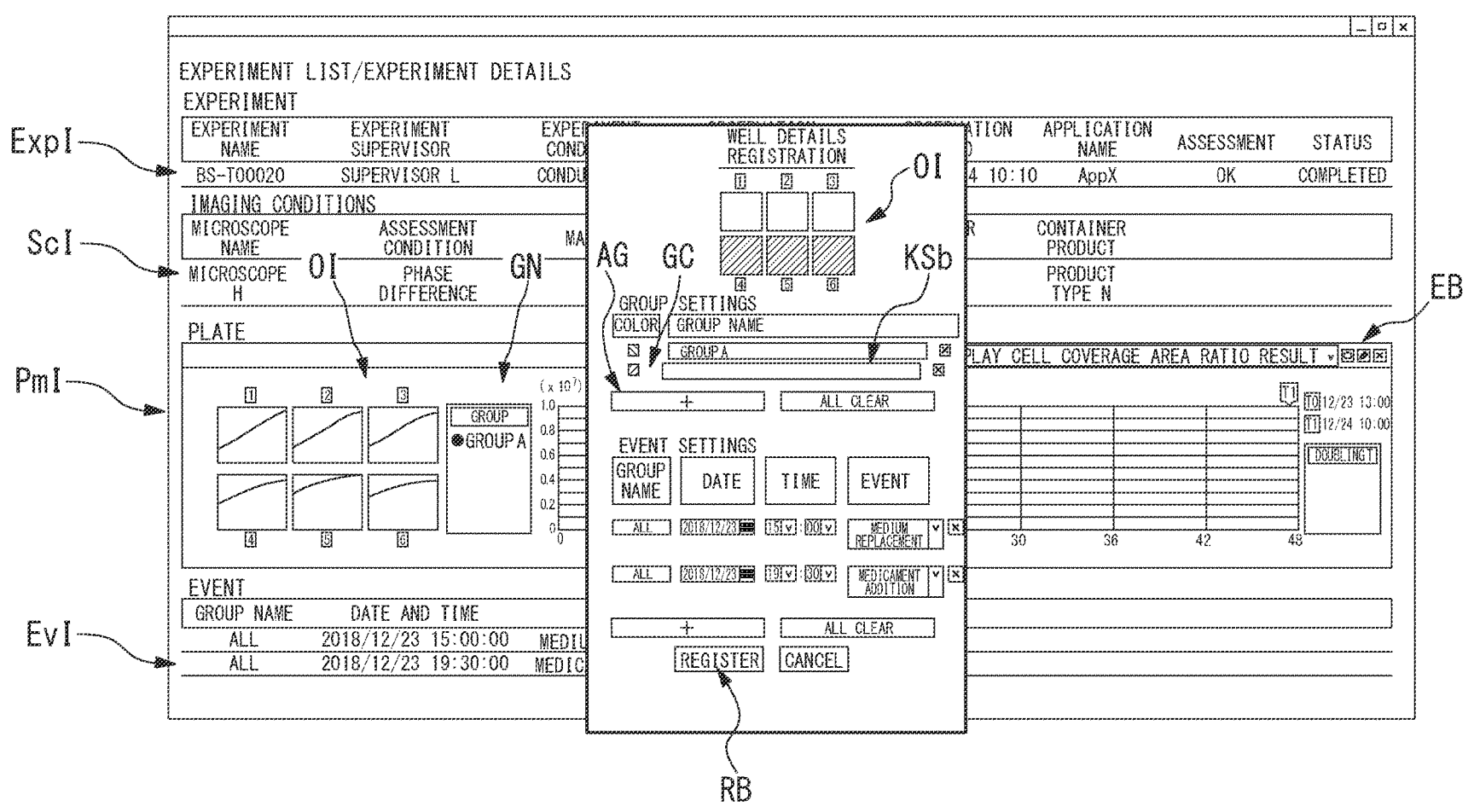

Next, the user operates the inputter 121 and presses an edit button EB (see FIG. 9) for a group registration. Here, editing includes editing group information by registering a new group. As shown in FIG. 9, the display controller 133 accepts a signal indicating that the edit button EB has been pressed. Then, as shown in FIG. 10, the display controller 133 displays a display image including observation image fields OI and a group add button AG for adding a new group. Next, as shown in FIG. 11, the user operates the inputter 121, selects two or more observation image fields OI corresponding to the storages to be added to the new group, and presses the group add button AG. Here, the display controller 133 displays a display image in which the observation image field OI is inverted with a predetermined color according to the selected observation image field OI. As a result, the display controller 133 receives a signal indicating the group add button AG having been pressed, and as shown in FIG. 12, the display controller 133 displays a display image including a text input field KSb for inputting (or editing) a group name for the new group and a register button RB for executing group registration. In addition, the display controller 133 highlights the observation image fields OI of the group registration target, using emphasizing information such as a color, a frame, and lines. In the vicinity of the text input field KSb there is arranged a group color content field GC that represents observation results and so forth in a different color for each group.

Figure 13:
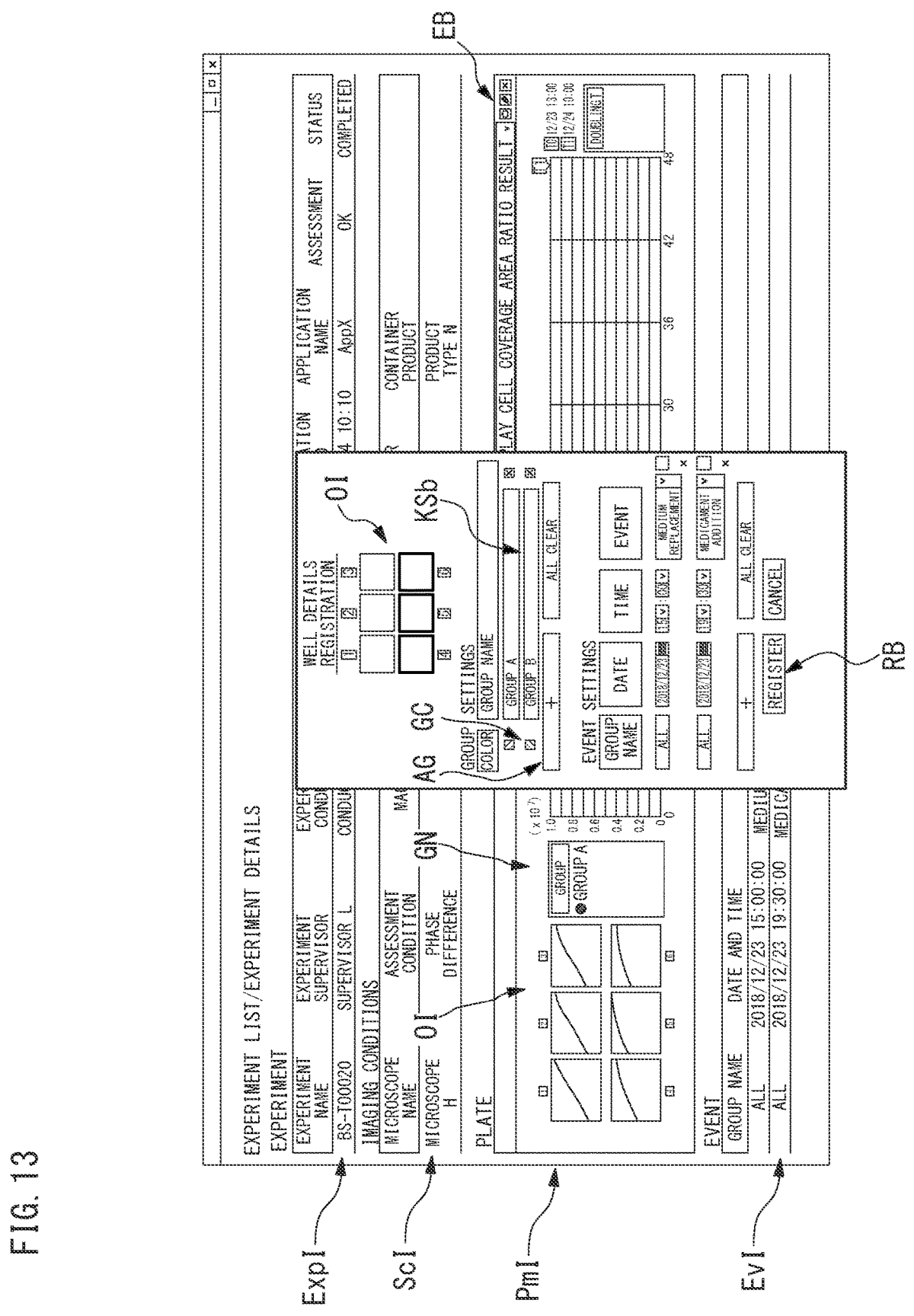
Figure 14:
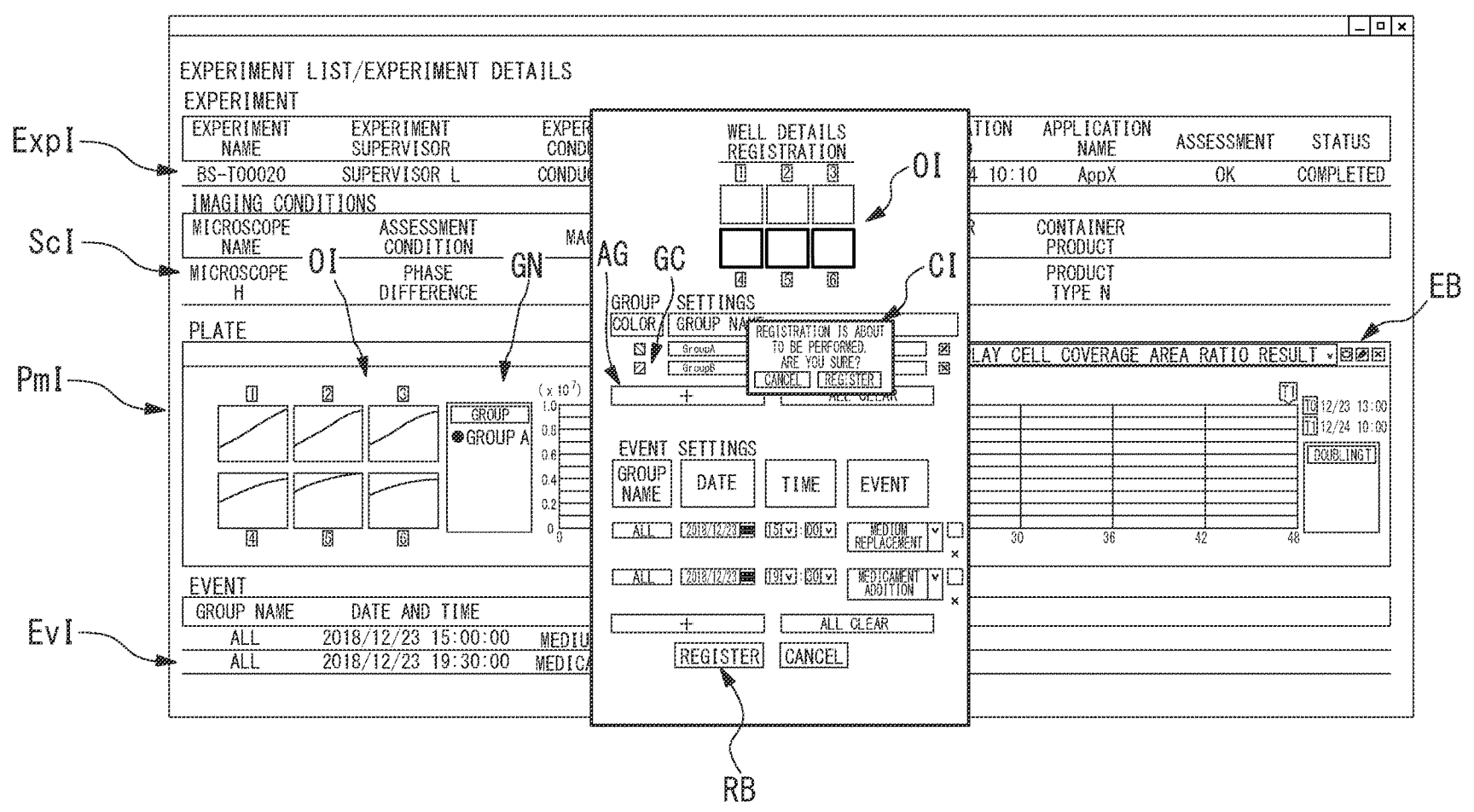
Figure 15:
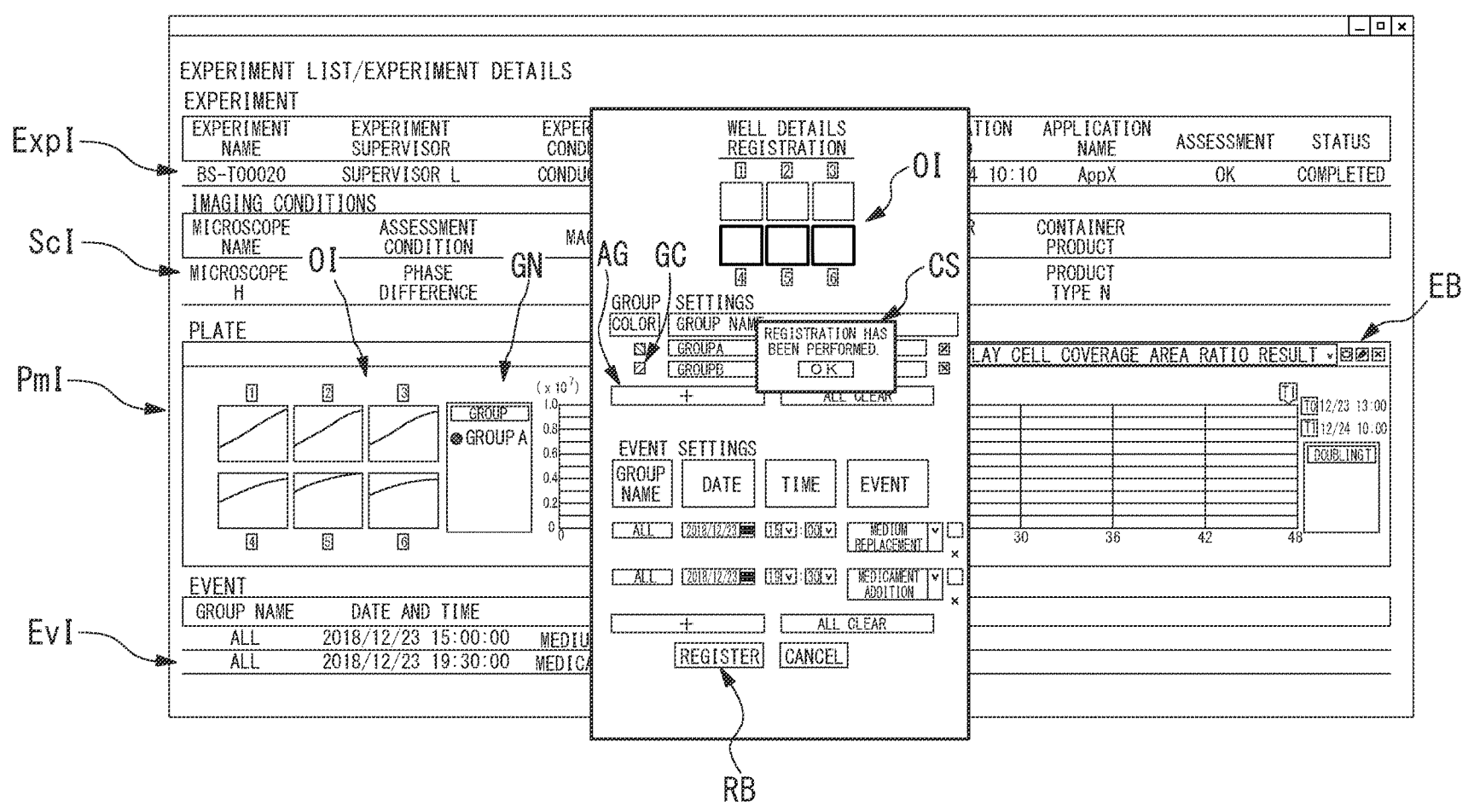

Next, as shown in FIG. 13, the user operates the inputter 121, makes a selection in the group color content field GC, inputs a group name to the text input field KSb, and presses the register button RB. As a result, the display controller 133 receives a signal indicating the register button RB having been pressed, and as shown in FIG. 14, the display controller 133 displays a display image including a confirmation image CI showing an image that confirms execution of group registration. When executing group registration using classification criteria, the user operates the inputter 121 and presses the registration button included in the confirmation image CI. On the other hand, when not executing group registration, the user operates the inputter 121 and presses a cancel button included in the confirmation image CI. As shown in FIG. 15, when the register button is pressed, the display controller 133 displays a display image including a completion image CS indicating the completion of the group registration. At this time, the registerer 135 stores group information related to the new group in the memory storage device 110.

Figure 16:
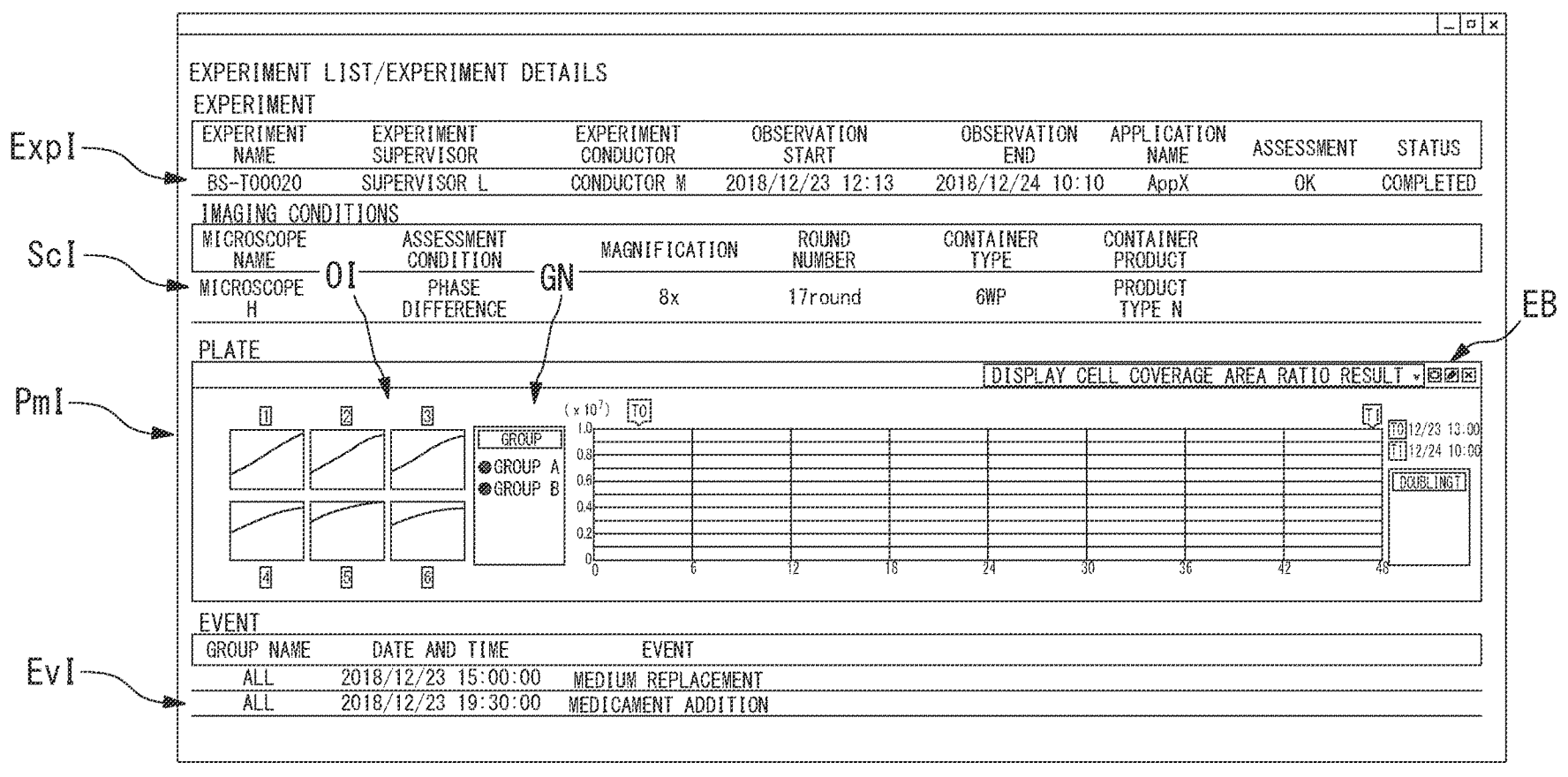
Figure 17:
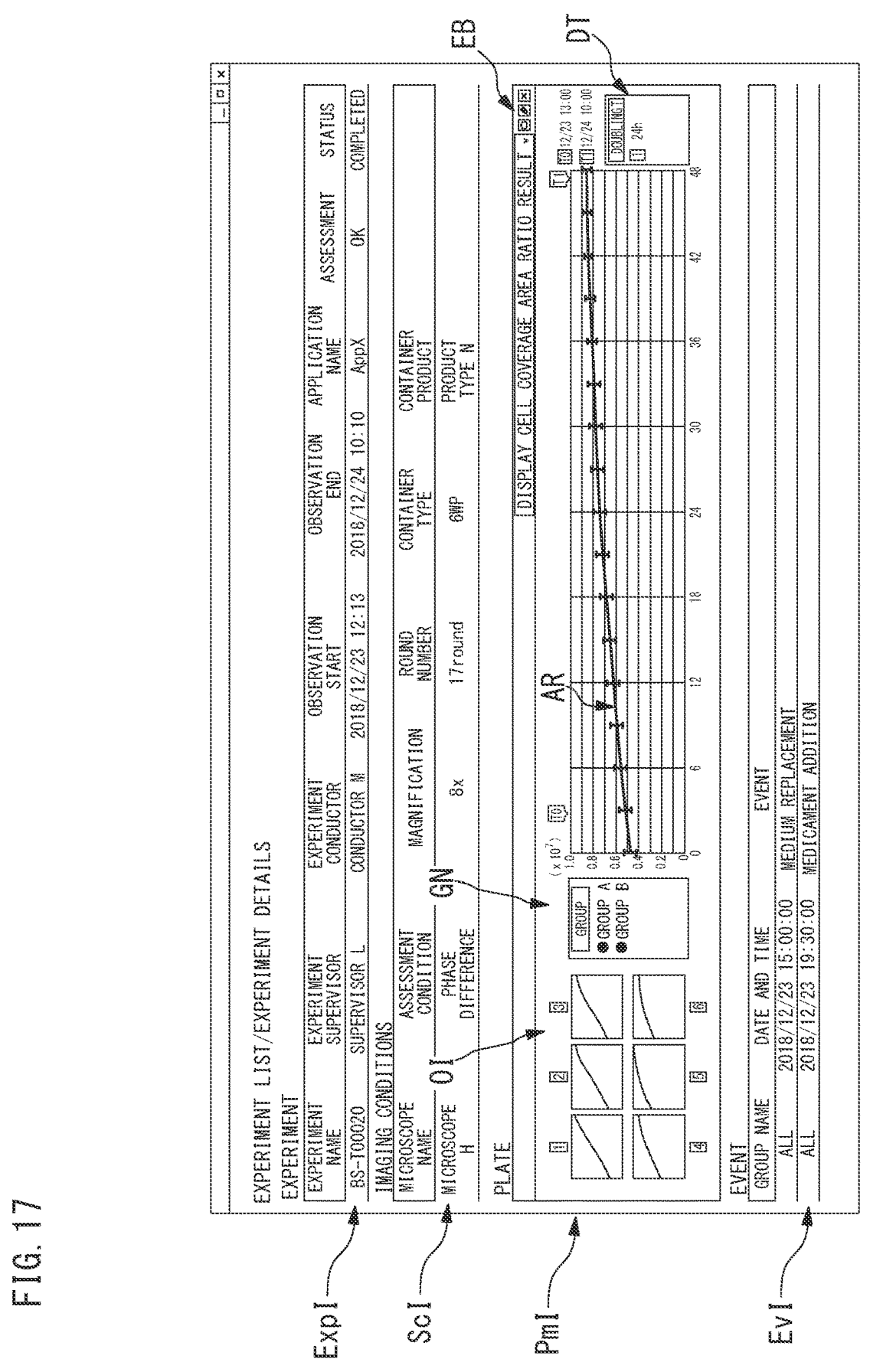

After that, as shown in FIG. 16, the display controller 133 displays a display image including the newly registered group name in the group name field GN in the plate map field PmI. Alternatively, the user operates the inputter 121 and selects a registered group from the group name field GN in the plate map field PmI. As a result, the display controller 133 receives a signal indicating a group having been selected from the group name field GN, and as shown in FIG. 17, the display controller 133 displays a display image including an analysis result field AR indicating the analysis result corresponding to the selected group name and the doubling time field DT that indicates a doubling time. For example, when displaying the analysis result field AR and the doubling time field DT, the display controller 133 accepts and displays a calculation processing result from the calculator 134. The analysis result field AR shown in FIG. 17 is an example of a visually representing the average number of target objects in the storages belonging to a group B, together with error bars. That is to say, the display controller 133 displays information that visually represents observation results on a display image, based on calculation executed by the calculator 134, and displays the display image on the display 122.

In the graph of the present embodiment (for example, the location where the analysis result field AR is displayed), data on the vertical axis and the horizontal axis of the graph are shown as an example. For example, the horizontal axis may display information related to times during the period from an observation start date and time to an observation end date and time. For example, vertical axis may display information for an item selected from the pull-down menu in the plate map field PmI. For example, when the number of cells is selected in the pull-down menu, the vertical axis represents values in a range such as 0 to 1.0 ($\times 10^7$). For example, when the cell coverage area ratio is selected in the pull-down menu, the vertical axis represents ratios in a range such as 0 to 100 (or 0 to 1.0). Therefore, the vertical axis and the horizontal axis of the graph change, depending on the displayed content.

Figure 18:
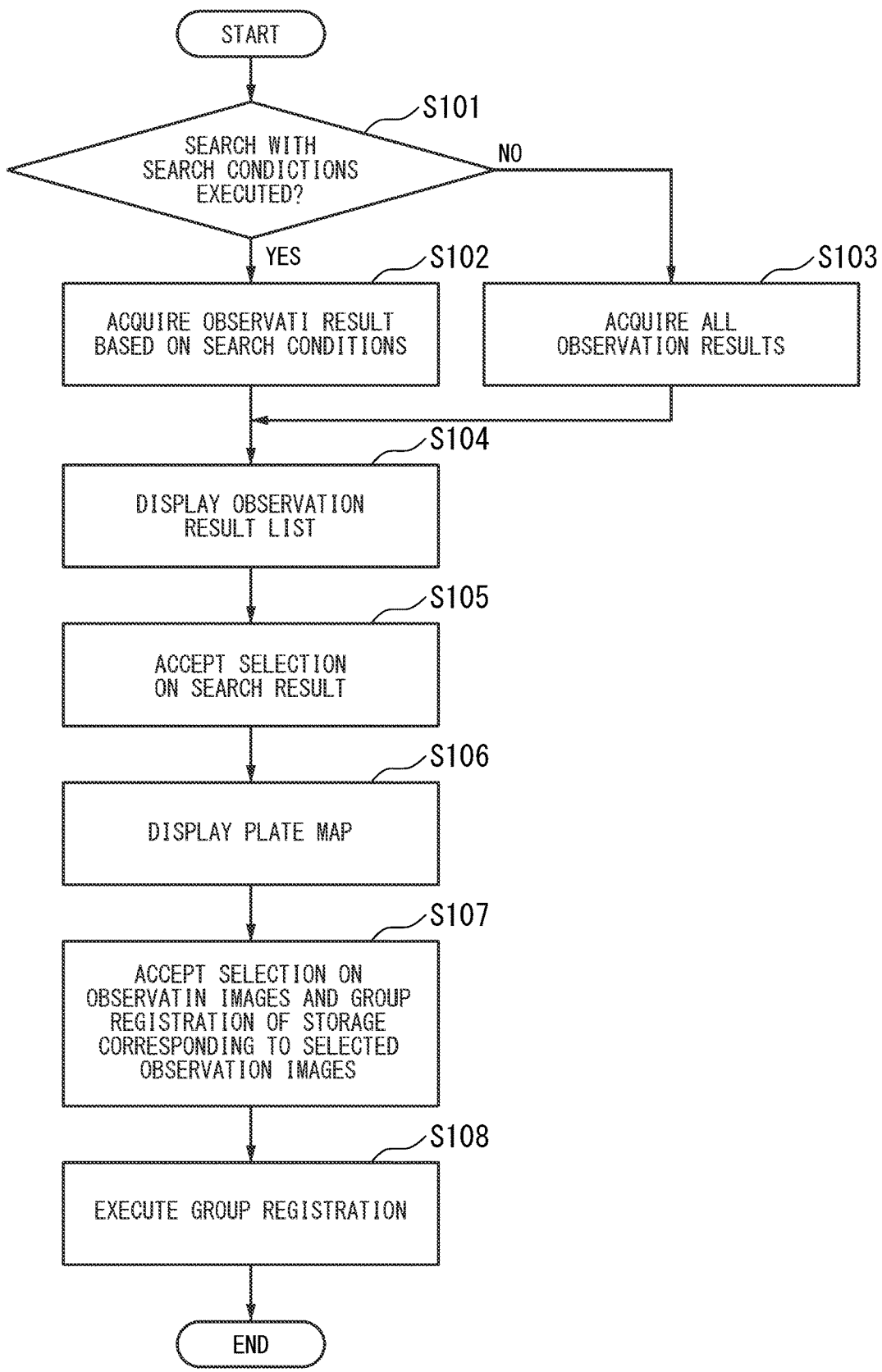
FIG. 18 is a flowchart showing an example of a flow of a process in the information processing device according to the first embodiment.

FIG. 18 is a flowchart showing an example of a process flow in the information processing device according to the first embodiment. In Step S101, the acquirer 132 determines whether a search has been executed with search conditions set therefor. For example, the acquisition unit 132 determines which one of the following types of searches has been executed. A search executed by inputting text in the text input field KSa and then pressing the search button SB; a search executed by selecting search conditions using the condition search fields FSa, FSb, FSc, and FSd and then pressing the search button SB; and a search executed only by pressing the search button SB. At this time, if the executed search is a search executed by inputting text in the text input field KSa and then pressing the search button SB or a search executed by selecting search conditions using the condition search fields FSa, FSb, FSc, and FSd and then pressing the search button SB (Step S101: Yes), the acquirer 132 executes the processing of Step S102. On the other hand, if the executed search is a search executed only by pressing the search button SB (Step S101: No), the acquirer 132 executes the process in Step S103.

In Step S102, the acquirer 132 acquires observation results based on the search conditions. For example, the acquirer 132 acquires observation results corresponding to the search conditions from the memory storage device 110 via the communicator 131. In Step S103, the acquirer 132 acquires all observation results. For example, the acquirer 132 acquires all observation results from the memory storage device 110 via the communicator 131. In Step S104, the display controller 133 displays a list of observation results. For example, the display controller 133 shows a list of observation results acquired by the acquirer 132 on a display image, and displays the display image on the display 122.

In Step S105, the display controller 133 accepts a selection of an observation result. For example, on the display image of an observation result list, the display controller 133 accepts the user's selection of an observation result as a signal. In Step S106, the display controller 133 displays a plate map. For example, the display controller 133 shows the observation result selected by the user, on a display image related to a container having a plurality of storages, and displays the display image on the display 122. At this time, the display controller 133 may show a graph or the like for the observation result on a display image on the basis of the result of calculation executed by the calculator 134, and display the display image on the display 122. The display controller 133 may show the time-series switching content field TS and the depth switching content field DP on a display image, and display the display image on the display 122.

In Step S107, the display controller 133 accepts a selection of observation images and a group registration of the storage corresponding to the selected observation images. For example, the display controller 133 accepts a signal indicating that the edit button EB has been pressed. The display controller 133 then displays on the display 122 a display image including the observation image fields OI and the group add button AG. Next, the display controller 133 accepts a signal indicating that a selection has been made from the observation image fields OI and the group add button AG has been pressed. At this time, the display controller 133 displays a display image in which the selected observation image field OI is inverted with a predetermined color. After that, the display controller 133 displays on the display 122 a display image including the text input field KSb for inputting a group name and the register button RB for executing the group registration. At this time, the observation image field OI of the group registration target may be highlighted a frame. Then, the display controller 133 accepts a signal indicating that a selection has been made in the group color content field GC, a group name has been input in the text input field KSb, and the register button RB has been pressed.

In Step S108, the registerer 135 executes the group registration. For example, the registerer 135 stores group information in the memory storage device 110 for the target observation results of the new group, based on the group color and the group name accepted by the display controller 133. Group registration is not limited to a new group registration. For example, as shown in FIG. 11, after selecting the observation image field OI, the user may select an existing group (here, "Group A") and press the registration button RB. As a result, the registerer 135 may store in the memory storage device 110 the group information to be added to the "Group A" for the selected storages.

Figure 19:
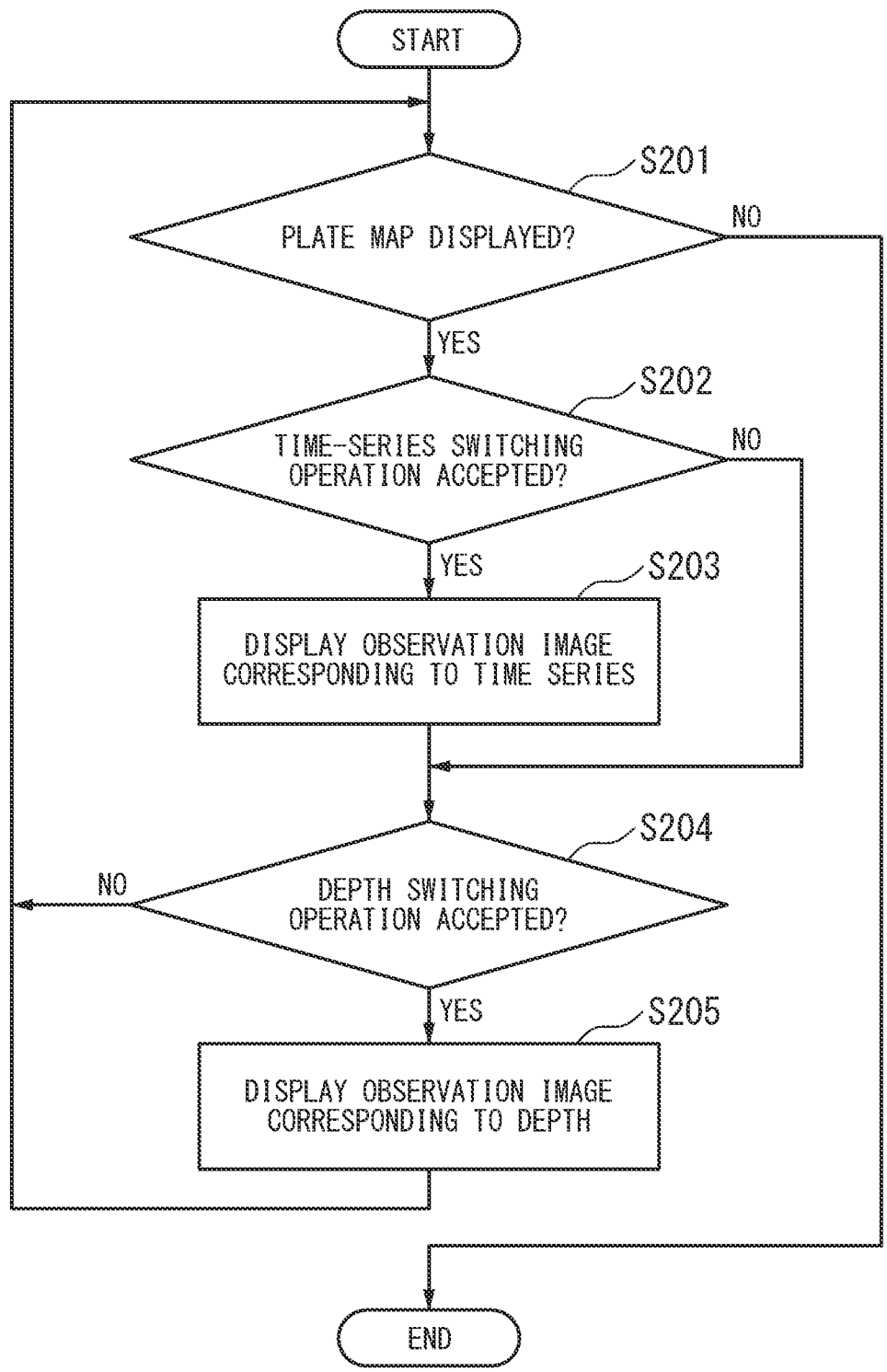
FIG. 19 is a flowchart showing an example of a flow of a process for switching observation image display according to the first embodiment.

FIG. 19 is a flowchart showing an example of a flow of a process for switching observation image display according to the first embodiment. In Step S201, the display controller 133 determines whether a plate map is being displayed. At this time, if a plate map is being displayed (Step S201: Yes), the display controller 133 executes the process of Step S202. On the other hand, if a plate map is not being displayed (Step S201: No), the display controller 133 ends the process because switching of observation image display does not need to be executed.

In Step S202, the display controller 133 determines whether a time-series switching operation has been accepted. For example, the display controller 133 determines whether a rectangle in the time-series switching content field TS is selected. The display controller 133 may determine whether an operation of moving the position of selected rectangle has been performed in the time-series switching content field TSa. Then, if a signal indicating a time-series switching operation has been accepted (Step S202: Yes), the display controller 133 displays an observation image corresponding to the time-series in Step S203. For example, the display controller 133 switches the display of the plate map field PmI, where the observation image corresponding to the period that corresponds to the position of the rectangle in the time-series switching content field TS serves as a display image. On the other hand, if a time-series switching operation has not been accepted (Step S202: No), the display controller 133 executes the process of Step S204.

In Step S204, the display controller 133 determines whether a depth switching operation has been accepted. For example, the display controller 133 determines whether a rectangle in the depth switching content field DP is selected. The display controller 133 may determine whether an operation of moving the position of selected rectangle has been performed in the depth switching content field DPa. Then, if a signal indicating a depth switching operation has been accepted (Step S204: Yes), the display controller 133 displays an observation image corresponding to the depth in Step S205. For example, when a rectangle in the depth switching content field DP is selected, the display controller 133 switches the display of the plate map field PmI using the observation image corresponding to the corresponding depth of the storage as a display image. On the other hand, if a depth switching operation has not been accepted (Step S204: No), the display controller 133 executes the process of Step S201. That is to say, in the case where a signal indicating an operation in the time-series switching content field TS or in the depth switching content field DP is accepted while the plate map is displayed, the display controller 133 executes the process of switching to and displaying the corresponding observation image.

Second Embodiment

Hereunder, a second embodiment will be described. In the present embodiment, the same reference signs are given to configurations similar to those in the embodiment described above, and the descriptions thereof may be omitted or simplified in some cases.

Figure 20:
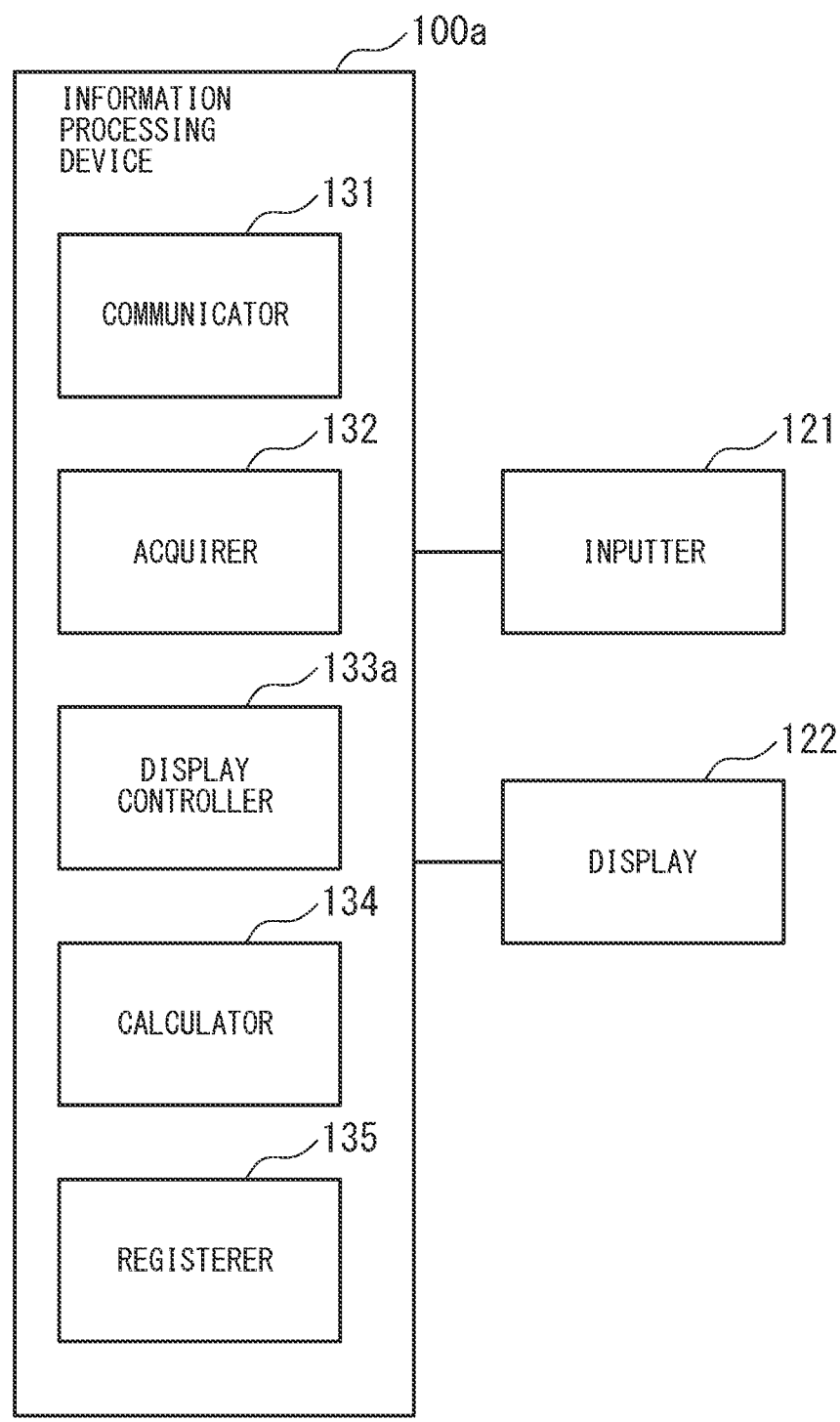
FIG. 20 is a block diagram showing a functional configuration example of the information processing device according to a second embodiment.

FIG. 20 is a block diagram showing a functional configuration example of an information processing device according to the second embodiment. As shown in FIG. 20, an information processing device 100a has a communicator 131, an acquirer 132, a display controller 133a, a calculator 134, and a registerer 135. An inputter 121 and a display 122 are connected to the information processing device 100a.

The acquirer 132 acquires observation results obtained by image-capturing a plurality of target objects under predetermined observation conditions. The process in the acquirer 132 is similar to that in the embodiment described above. In a display image related to a container having a plurality of storages respectively storing the plurality of target objects, the display controller 133a highlights storages of the container that belong to a group meeting the above classification criterion selected by the user, using emphasizing information such as a color, a frame, or lines. For example, the display controller 133a displays on the display 122 a display image including a plate map having a group name. Then, the display controller 133a accepts a signal indicating user's operation having been performed on the display image to select a group name. Then, the display controller 133a highlights, on the display image related to the container, the storages of the container belonging to the group selected by the user, and displays the highlighted display image on the display 122. The display controller 133a switches highlighting of the storages of the container that belong to the corresponding group, according to the selection of a classification criterion made by the user (for example, a signal indicating that a classification criteria has been selected). For example, in the case where a signal indicating the user having selected one first classification criterion of a plurality of classification criteria (may be referred to as a plurality of groups) has been detected, the display controller 133a highlights storages of the container that belong to a group meeting the first classification criterion. Next, in the case where a signal indicating the user having selected another second classification criterion, which is different from the first classification criterion, has been subsequently detected, the display controller 133a switches highlighting so as to highlight storages of the container that belong to a group meeting the second classification criterion.

FIG. 21 is a diagram showing an example of a plate map according to the second embodiment. In FIG. 21, a case of a 96 well-plate is taken as an example. As shown in FIG. 21, the display controller 133a displays a display image in which storages of the container belonging to the same group are highlighted in a color on the plate map. The storages shown in FIG. 21 are represented using effects for the sake of convenience of description, however, in reality, they would be represented in different colors. The color of the storages may correspond to the group color described above. For example, storages with an anti-drying buffer fluid arranged on the outer side of the container is shown in gray on the display image. For example, storages represented with a grid effect in the container is shown in red on the display image. For example, storages represented with vertical lines in the container is shown in green on the display image. For example, storages represented with horizontal lines in the container is shown in blue on the display image. For example, on the display image, the display controller 133a shows a graph indicating the number of target objects in each group as information of observation result analysis. In the graphs also, the display controller 133a shows the solid line in red (corresponding to the storages with the grid effect), the broken line in green (corresponding to the storages with the vertical lines effect), and the chained line in blue (corresponding to the storages with the horizontal lines effect). The graphs shown in FIG. 21 show the average values of the number of target objects in the storages included in each group.

Figure 22:
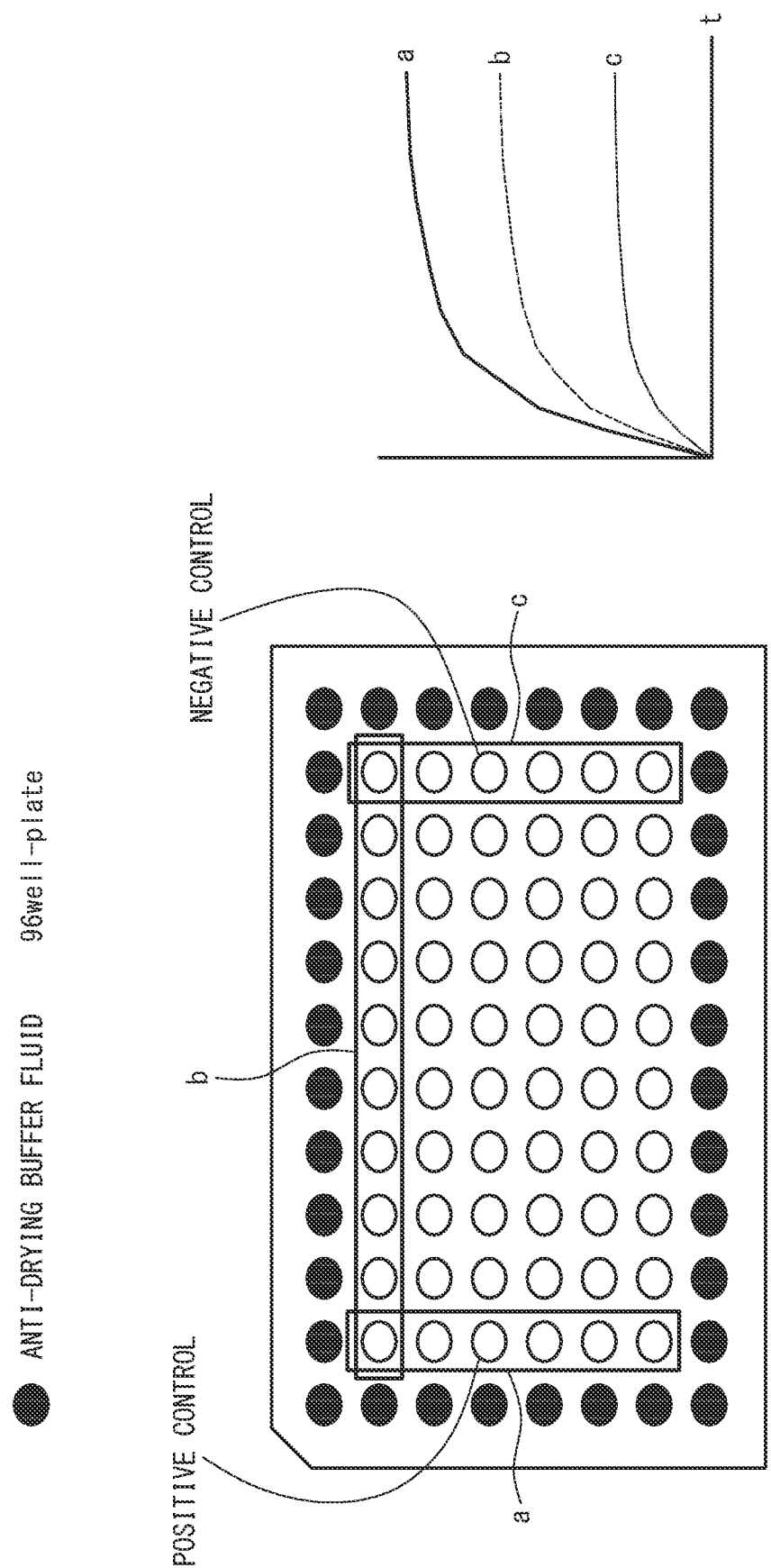
FIG. 22 is a diagram showing an example of a plate map according to the second embodiment.

FIG. 22 is a diagram showing an example of a plate map according to the second embodiment. As shown in FIG. 22, the display controller 133a displays a display image in which storages of the container belonging to the same group are highlighted in a frame on the plate map. The frame a corresponds to a group (indicated in red) with the grid effect shown in FIG. 21. The frame b corresponds to a group (indicated in green) with the vertical lines effect shown in FIG. 21. The frame c corresponds to a group (indicated in blue) with the horizontal lines effect shown in FIG. 21. The displayed graphs are presented to respectively correspond to the frame a, the frame b, and the frame c. Highlighting the same group in a color and highlighting it in a frame may be practiced at the same time.

Figure 23:
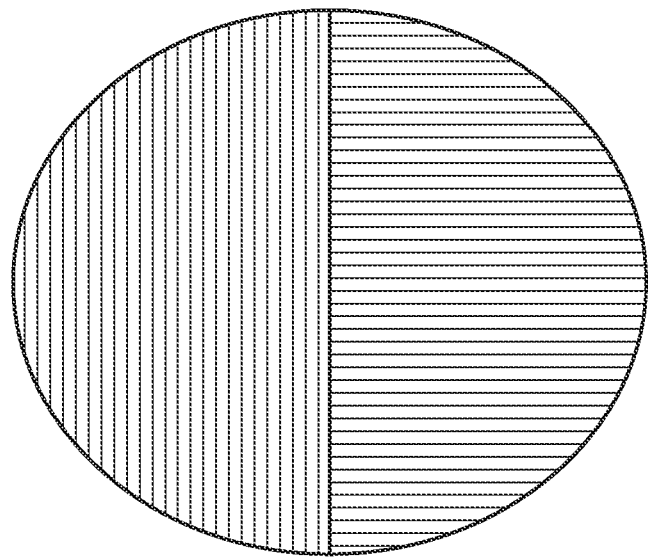
FIG. 23 is a diagram showing an example of highlighting a storage according to the second embodiment.
Figure 24:
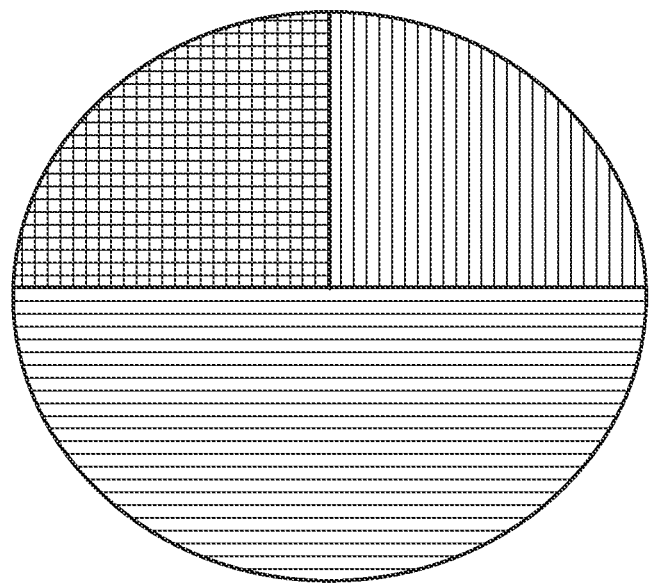
FIG. 24 is a diagram showing an example of highlighting the storage according to the second embodiment.

In addition to the above examples, there are various other ways to highlight storages. FIG. 23 to FIG. 26 are diagrams each showing an example of highlighting the storages according to the second embodiment. As shown in FIG. 23 and FIG. 24, when there is a storage that belongs to a plurality of groups meeting classification criteria, the display controller 133a shows the storage with a combination of colors each corresponding to the group to which it belongs. For example, in FIG. 23, the portion with the vertical lines effect is shown in green, and the portion with the horizontal lines effect is shown in blue. For example, in FIG. 24, the portion with the grid effect is shown in red, and the portion with the vertical lines effect is shown in green, and the portion with the horizontal lines effect is shown in blue. In FIG. 24, the group corresponding to a negative control group (group shown in blue) in which the user is primarily interested to confirm is expressed more broadly than the other groups.

Figure 25:
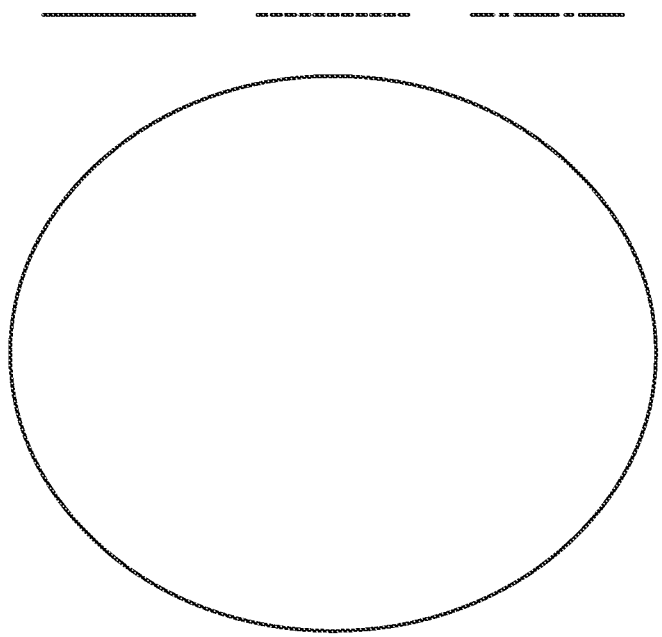
FIG. 25 is a diagram showing an example of highlighting the storage according to the second embodiment.
Figure 26:
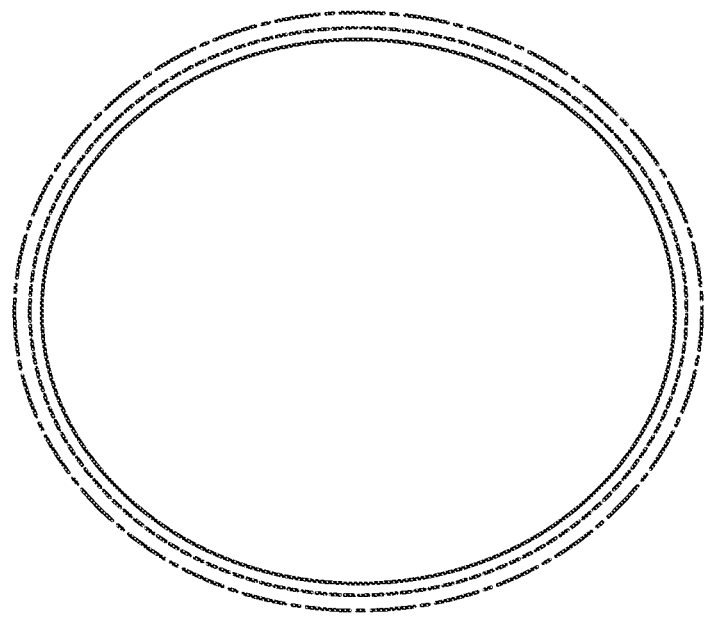
FIG. 26 is a diagram showing an example of highlighting the storage according to the second embodiment.

As shown in FIG. 25 and FIG. 26, the display controller 133a displays a display image in which a content indicating the group to which the storage belongs is added and highlighted in the vicinity of the storage. For example, in FIG. 25 and FIG. 26, the solid line is shown in red (corresponding to the storage with the grid effect), the broken line in green (corresponding to the storage with the vertical lines effect), and the chained line in blue (corresponding to the storage with the horizontal lines effect). That is to say, the storages in FIG. 25 and FIG. 26 each represent that the storage belongs to three groups. The highlighting and the graphs corresponding to storages of the same group switched and displayed when other classification criteria are selected as described above.

Figure 27:
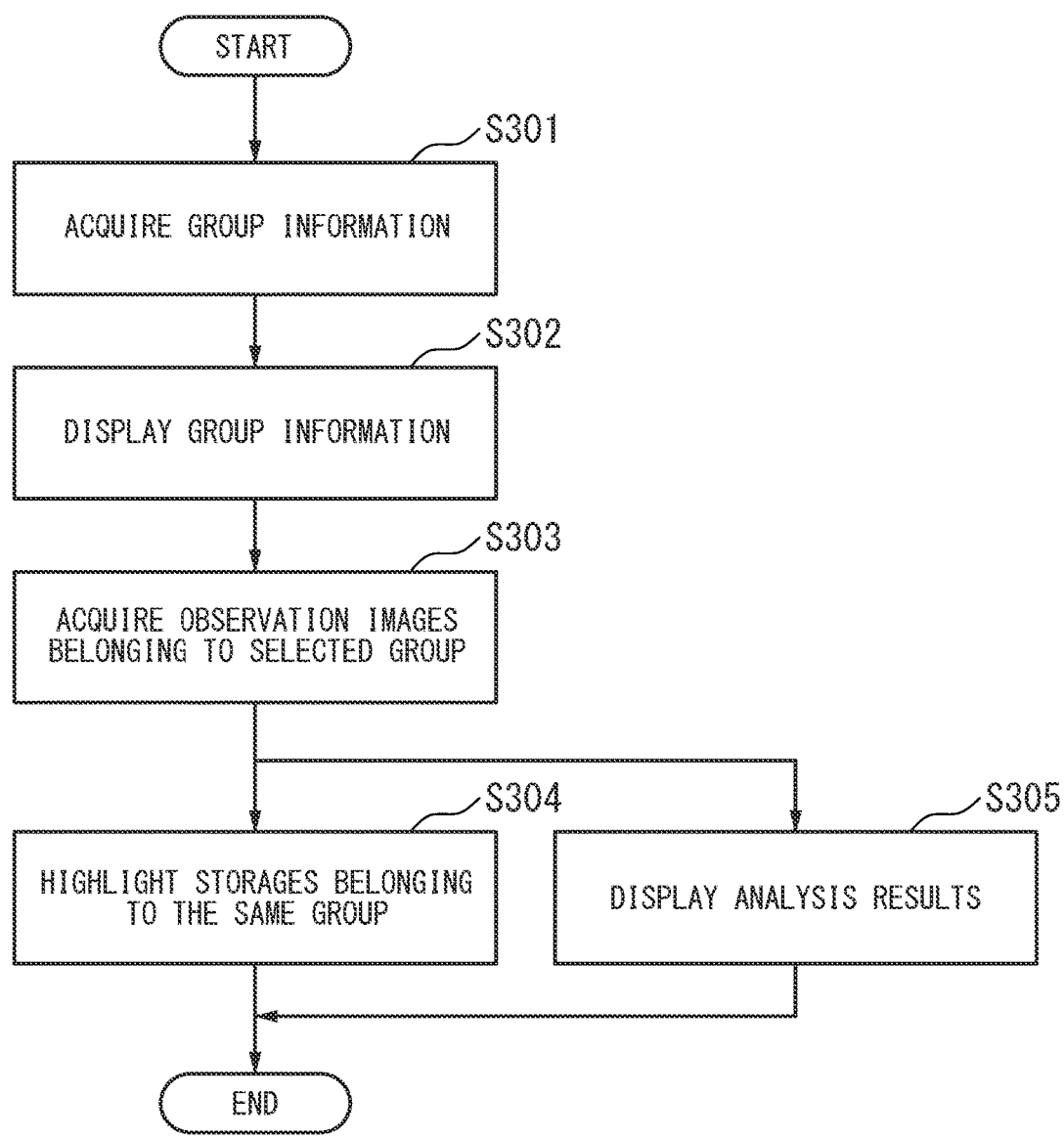
FIG. 27 is a flowchart showing an example of a flow of a process in the information processing device according to the second embodiment.

FIG. 27 is a flowchart showing an example of a process flow in the information processing device according to the second embodiment. In FIG. 27, the process flow in a situation where a plate map is being displayed is described.

In Step S301, the acquirer 132 acquires from the memory storage device 110 information related to observation results of each group. In Step S302, the display controller 133a displays on the display 122 a display image including the information related to the observation results of each group acquired by the acquirer 132. Here, the user operates the inputter 121 to select an arbitrary group. The user may select a plurality of groups or select one group only.

In Step S303, the acquirer 132 acquires from the memory storage device 110 observation results including observation images that belongs to the group selected by the user. In step S304, if a plurality of groups are selected, the display controller 133a highlights the storages that belong to the same group. For example, the display controller 133a generates a display image that highlights the storages belonging to the same group, and displays the generated display image on the display 122. In step S305, if a single group is selected, the display controller 133a displays the analysis results of observation results related to this group. For example, the display controller 133a displays on the display 122 a display image including information that graphically represents the observation results on the plate map, based on the calculation results of the calculator 134.

Third Embodiment

Hereunder, a third embodiment will be described. In the present embodiment, the same reference signs are given to configurations similar to those in the embodiment described above, and the descriptions thereof may be omitted or simplified in some cases.

Figure 28:
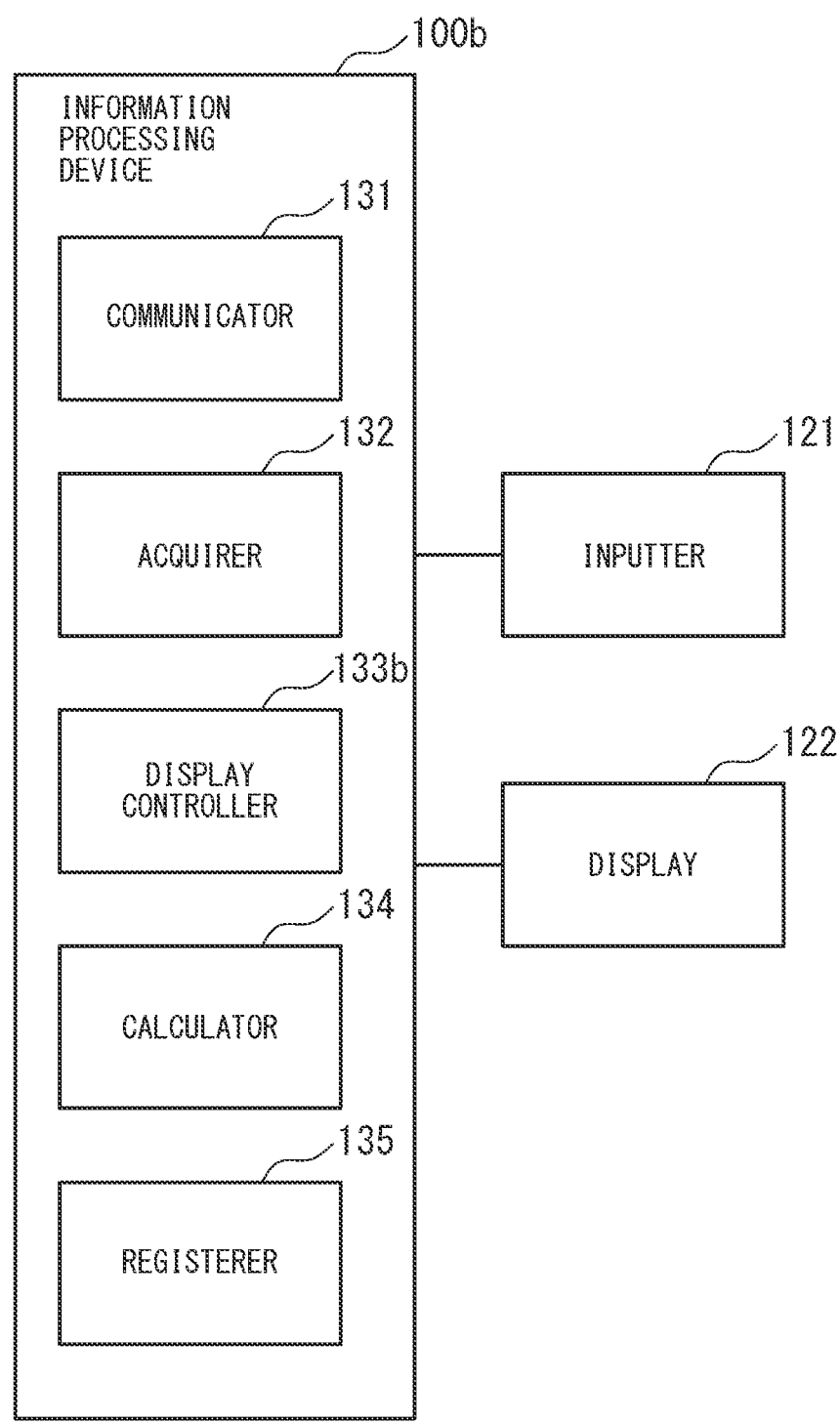
FIG. 28 is a block diagram showing a functional configuration example of an information processing device according to a third embodiment.

FIG. 28 is a block diagram showing a functional configuration example of an information processing device according to the third embodiment. As shown in FIG. 28, an information processing device 100b has a communicator 131, an acquirer 132, a display controller 133b, a calculator 134, and a registerer 135. An inputter 121 and a display 122 are connected to the information processing device 100b.

On a display image, the display controller 133b highlights the storages of the container corresponding to the observation conditions or the observation results specified by the user. For example, after having highlighted storages belonging to the same group, the display controller 133b accepts the user's specification on the observation conditions or the observation results. That is to say, after having confirmed the observation results of the plurality of groups, the user further specifies observation conditions or observation results in order to confirm the storages corresponding to arbitrary information of observation results and observation results. For example, storages belonging to the same group does not always mean the same medicament is used, and even if the same medicament is used, it does not always mean storages are registered to the same group. Therefore, in the present embodiment, regardless of the group (classification criterion), a process for confirming (narrowing down) storages corresponding to any condition is executed. The display controller 133b displays on the display 122 a display image highlighting the storages corresponding to the specified observation conditions or observation results. The method of highlighting may be realized by at least one or more of using a color, using a frame, and an added content. After storages have been highlighted, a group registration may be performed according to operations of the user if the group registration has not been done.

FIG. 29 is a diagram showing an example of a plate map according to the third embodiment. In FIG. 29, a case of highlighting storages corresponding to a certain type of serum and highlighting storages corresponding to a certain concentration of serum is taken as an example. As shown in FIG. 29, the display controller 133b displays a display image in which storages of the container that correspond to the serum type and serum concentration specified by the user are highlighted in a color and a frame on the plate map. The storages shown in FIG. 29 are represented using effects for the sake of convenience of description, however, in reality, they would be represented in different colors. For example, storages with an anti-drying buffer fluid arranged on the outer side of the container is shown in gray on the display image. For example, storages represented with a grid effect in the container is shown in red on the display image. For example, storages represented with vertical lines in the container is shown in green on the display image. For example, on the display image, the display controller 133b shows a graph indicating the number of target objects for each observation condition target and observation result target, as information of observation result analysis. In the graphs also, the display controller 133b shows the solid line in red (corresponding to the storages with the grid effect), and the broken line in green (corresponding to the storages with the vertical lines effect).

Figure 30:
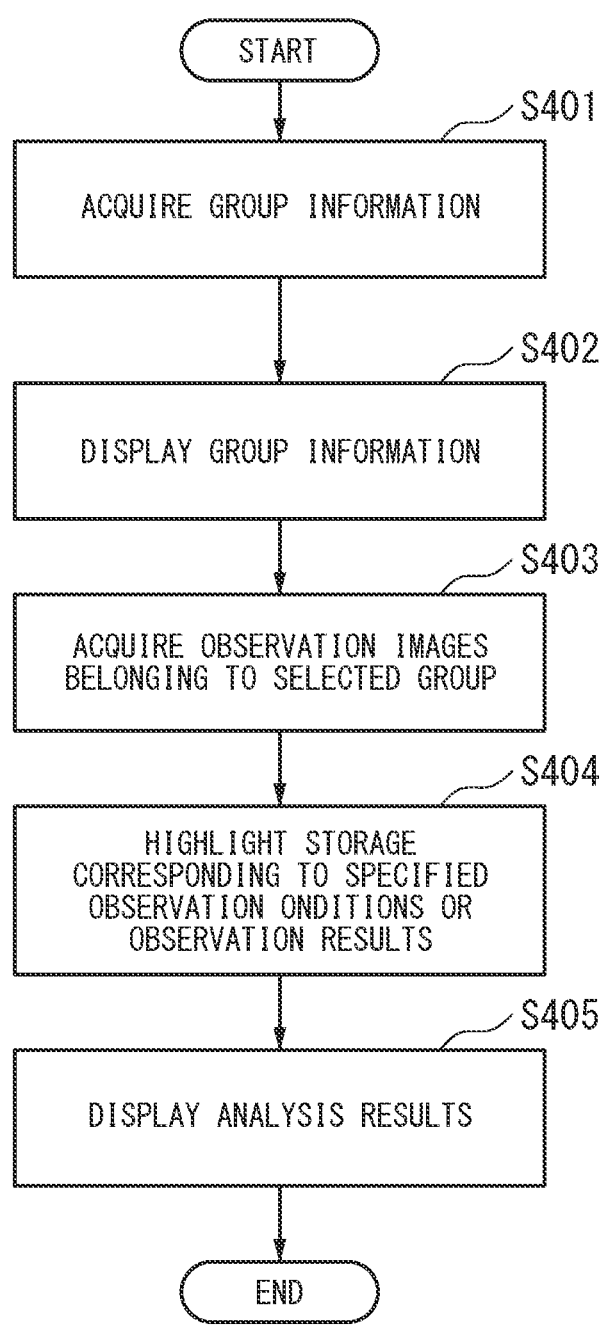
FIG. 30 is a flowchart showing an example of a flow of a process in the information processing device according to the third embodiment.

FIG. 30 is a flowchart showing an example of a process flow in the information processing device according to the third embodiment. In FIG. 30, the process flow in a situation where a plate map is being displayed is described. In Step S401, the acquirer 132 acquires from the memory storage device 110 information related to observation results of each group. In Step S402, the display controller 133b displays on the display 122 a display image including the information related to the observation results of each group acquired by the acquirer 132. Here, the user operates the inputter 121 to select an arbitrary group. The user may select a plurality of groups or select one group only.

In Step S403, the acquirer 132 acquires from the memory storage device 110 observation results including observation images that belongs to the group selected by the user. Here, the user operates the inputter 121 and specifies observation conditions or observation results to be confirmed. In Step S404, the display controller 133b displays a display image that highlights the storages corresponding to the observation conditions or observation results specified by the user. In Step S405, the display controller 133b displays observation results. For example, upon accepting a signal indicating the user having specified observation conditions or observation results, the display controller 133b displays on the display 122 a display image that indicates the storages corresponding to each observation condition or each observation result, with a color, a frame, or an added content. The display controller 133b also displays at the same time on the display 122 analysis results related to the corresponding storages.

Fourth Embodiment

Hereunder, a fourth embodiment will be described. In the present embodiment, the same reference signs are given to configurations similar to those in the embodiment described above, and the descriptions thereof may be omitted or simplified in some cases.

Figure 31:
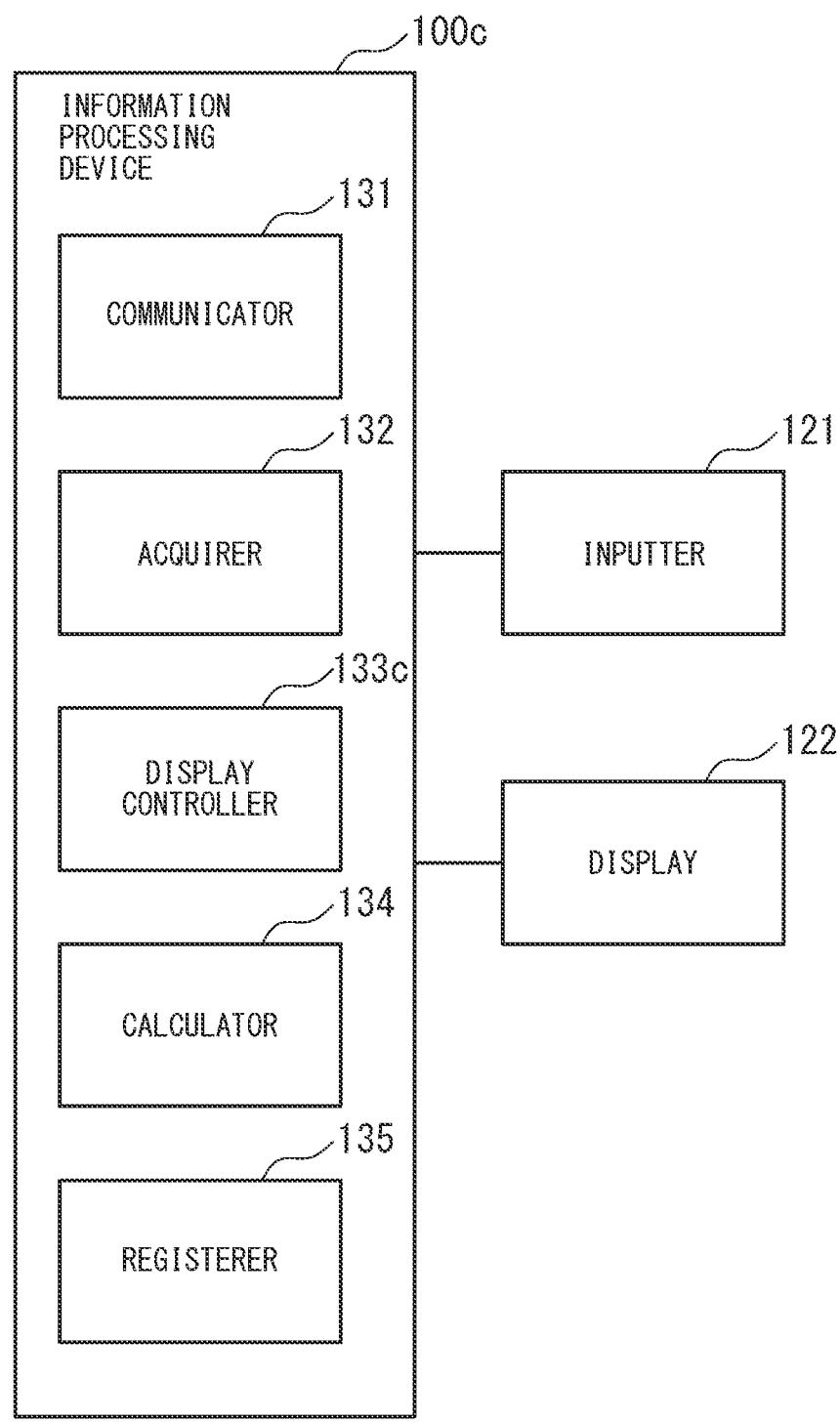
FIG. 31 is a block diagram showing a functional configuration example of an information processing device according to a fourth embodiment.

FIG. 31 is a block diagram showing a functional configuration example of an information processing device according to the fourth embodiment. As shown in FIG. 31, an information processing device 100c has a communicator 131, an acquirer 132, a display controller 133c, a calculator 134, and a registerer 135. An inputter 121 and a display 122 are connected to the information processing device 100c.

On a display image, the display controller 133c highlights the storages of the container according to a threshold value condition specified by the user. For example, after having highlighted storages belonging to the same group, the display controller 133c accepts a signal indicating the user's specification on the threshold value condition. That is to say, after having confirmed observation results of a plurality of groups, the user further specifies a threshold value condition in order to confirm the storages corresponding to the threshold value condition. In the present embodiment, regardless of the group (classification criterion), a process for confirming storages corresponding to any threshold value condition is executed. The display controller 133c displays on the display 122 a display image highlighting the storages corresponding to the specified threshold value condition. The method of highlighting may be realized by at least one or more of using a color and added content. After storages have been highlighted, a group registration may be performed according to operations of the user if the group registration has not been done.

The display controller 133c adds to the display image a content for adjusting the threshold value condition. After specifying a threshold value condition, the user can further change the threshold value condition while confirming the display image. The display controller 133c displays on the display 122 a display image that highlights the storages corresponding to the changed threshold value condition.

FIG. 32 is a diagram showing an example of a plate map according to the fourth embodiment. In FIG. 32, a case of applying a measuring application A and a measuring application B is taken as an example. As shown in FIG. 32, the display controller 133c displays a display image in which storages are highlighted on the plate map with a color or an added content according to the specified threshold value condition. The storages shown in FIG. 32 are represented using effects for the sake of convenience of description, however, in reality, they would be represented in different colors. For example, storages with an anti-drying buffer fluid arranged on the outer side of the container is shown in gray on the display image. For example, storages represented with a grid effect in the container is shown in red on the display image. For example, storages represented with vertical lines in the container is shown in green on the display image. As analysis information of observation results, the display image shows graphs indicating the number of target objects in storages corresponding to each of the measuring application A and the measuring application B. In the graphs also, the display controller 133c shows the solid line in red (corresponding to the storages with the grid effect), and the broken line in green (corresponding to the storages with the vertical lines effect).

Figure 33:
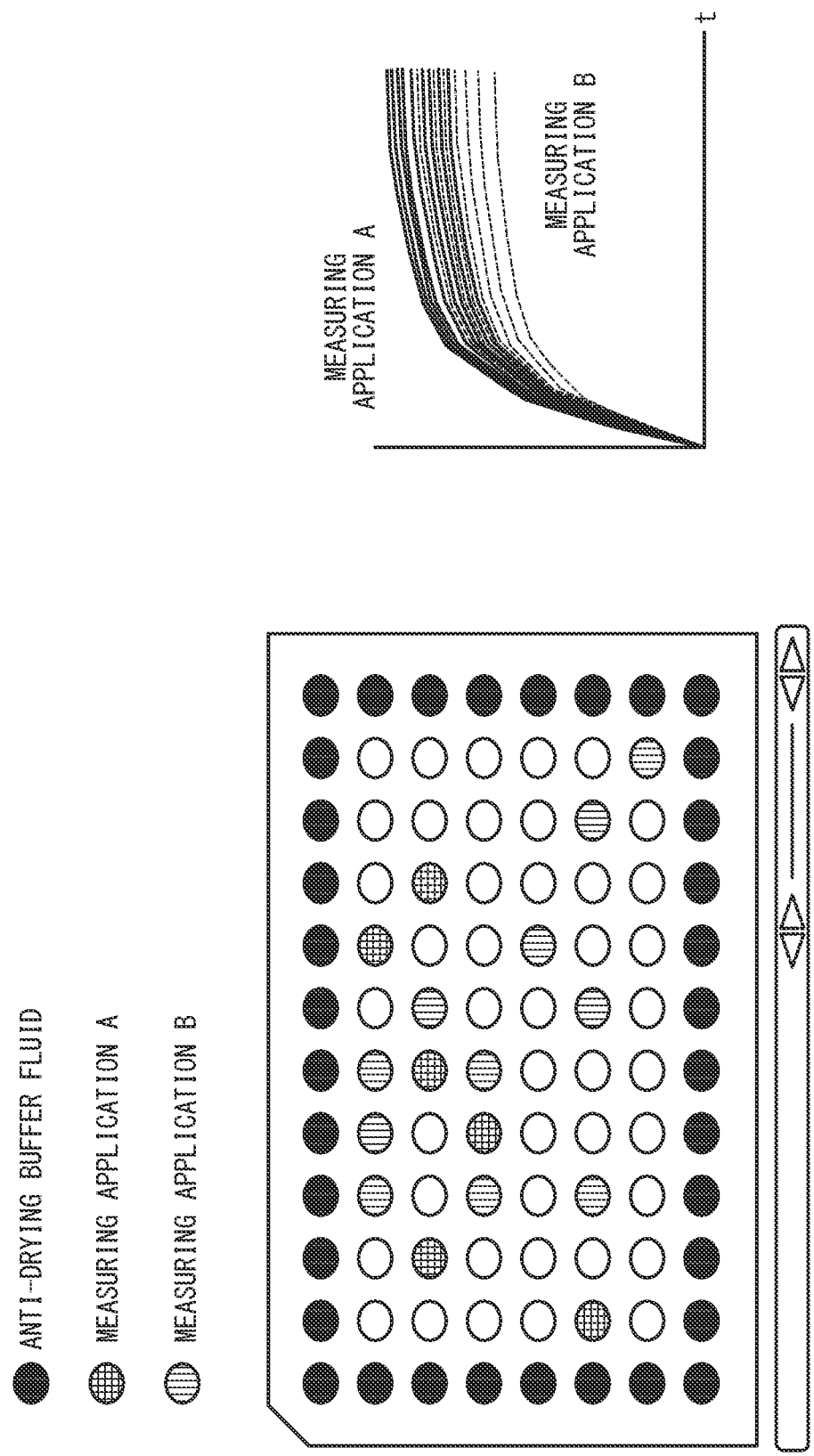
FIG. 33 is a diagram showing an example of a plate map according to the fourth embodiment.

FIG. 33 is a diagram showing an example of a plate map according to the fourth embodiment. As shown in FIG. 33, the display controller 133c displays a display image in which a content is added for adjusting the threshold value condition. The user changes the threshold value condition. As a result, the display controller 133c displays a display image that highlights the storages corresponding to the changed threshold value condition (for example, several storages of the group matching the threshold value condition).

Figure 34:
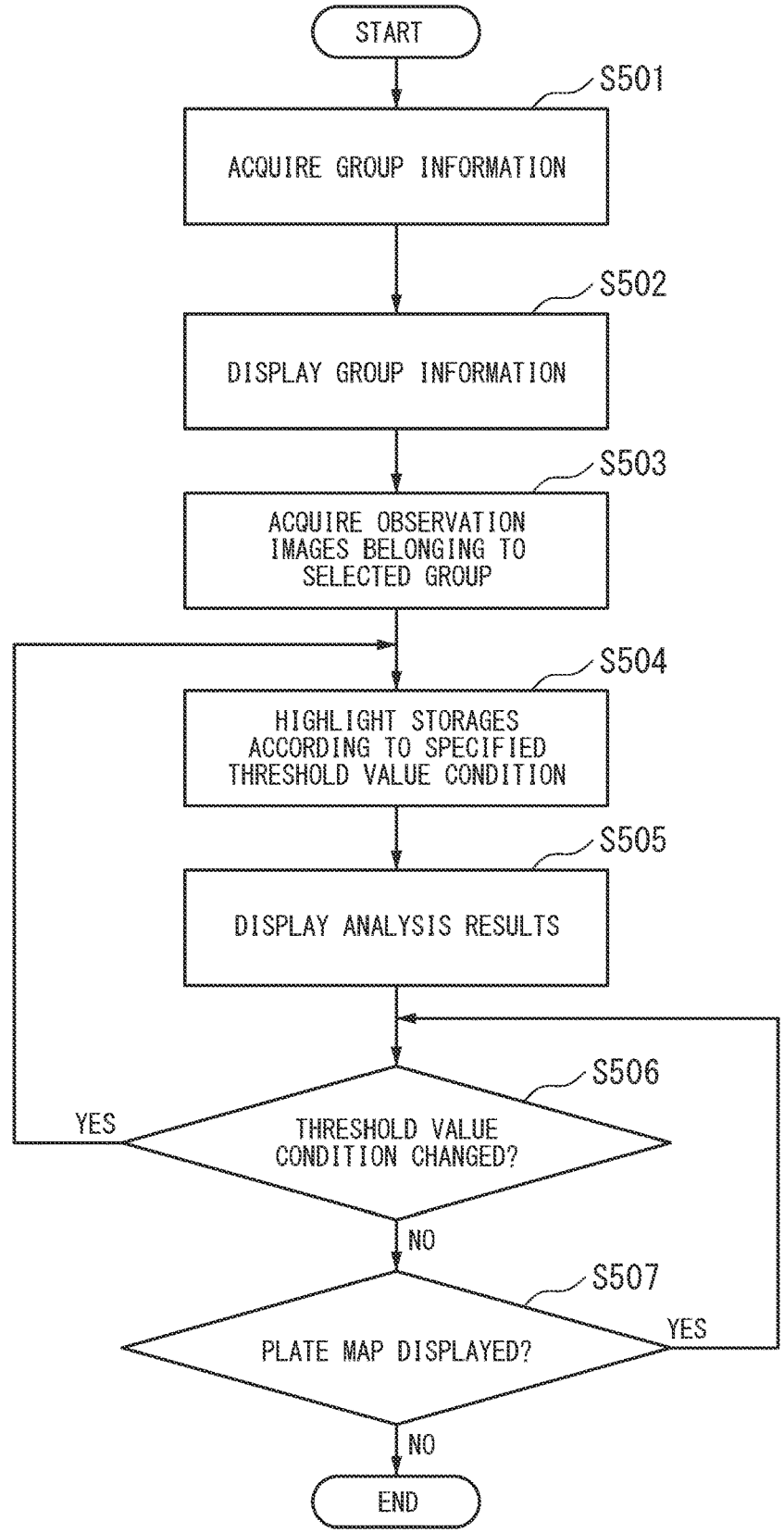
FIG. 34 is a flowchart showing an example of a flow of a process in the information processing device according to the fourth embodiment.

FIG. 34 is a flowchart showing an example of a process flow in the information processing device according to the fourth embodiment. In FIG. 34, the process flow in a situation where a plate map is being displayed is described. In Step S501, the acquirer 132 acquires from the memory storage device 110 information related to observation results of each group. In Step S502, the display controller 133c displays on the display 122 a display image including the information related to the observation results of each group acquired by the acquirer 132. Here, the user operates the inputter 121 to select an arbitrary group. The user may select a plurality of groups or select one group only.

In Step S503, the acquirer 132 acquires from the memory storage device 110 observation results including observation images that belongs to the group selected by the user. Here, the user operates the inputter 121 and specifies the threshold value condition to be confirmed. In Step S504, the display controller 133c highlights the storages corresponding to the threshold value condition specified by the user. The display controller 133c displays observation results. For example, the display controller 133c displays a display image that highlights the storages corresponding to the specified threshold value condition, and that indicates the analysis results of observation results of the highlighted storages.

In Step S506, the display controller 133c determines whether the threshold value condition has been changed. For example, if a signal indicating an operation on a content added to the display image that changes the threshold value condition has been accepted (Step S506: Yes), the display controller 133c executes the process of Step S504. On the other hand, if an operation on a content added to the display image that changes the threshold value condition has not been accepted (Step S506: No), whether a plate map is being displayed is determined in Step S507. If a plate map is being displayed (Step S507: Yes), the display controller 133c executes the process of Step S506. On the other hand, if a plate map is not being displayed (Step S507: No), the display controller 133c ends the process.

Fifth Embodiment

Hereunder, a fifth embodiment will be described. In the present embodiment, the same reference signs are given to configurations similar to those in the embodiment described above, and the descriptions thereof may be omitted or simplified in some cases.

Figure 35:
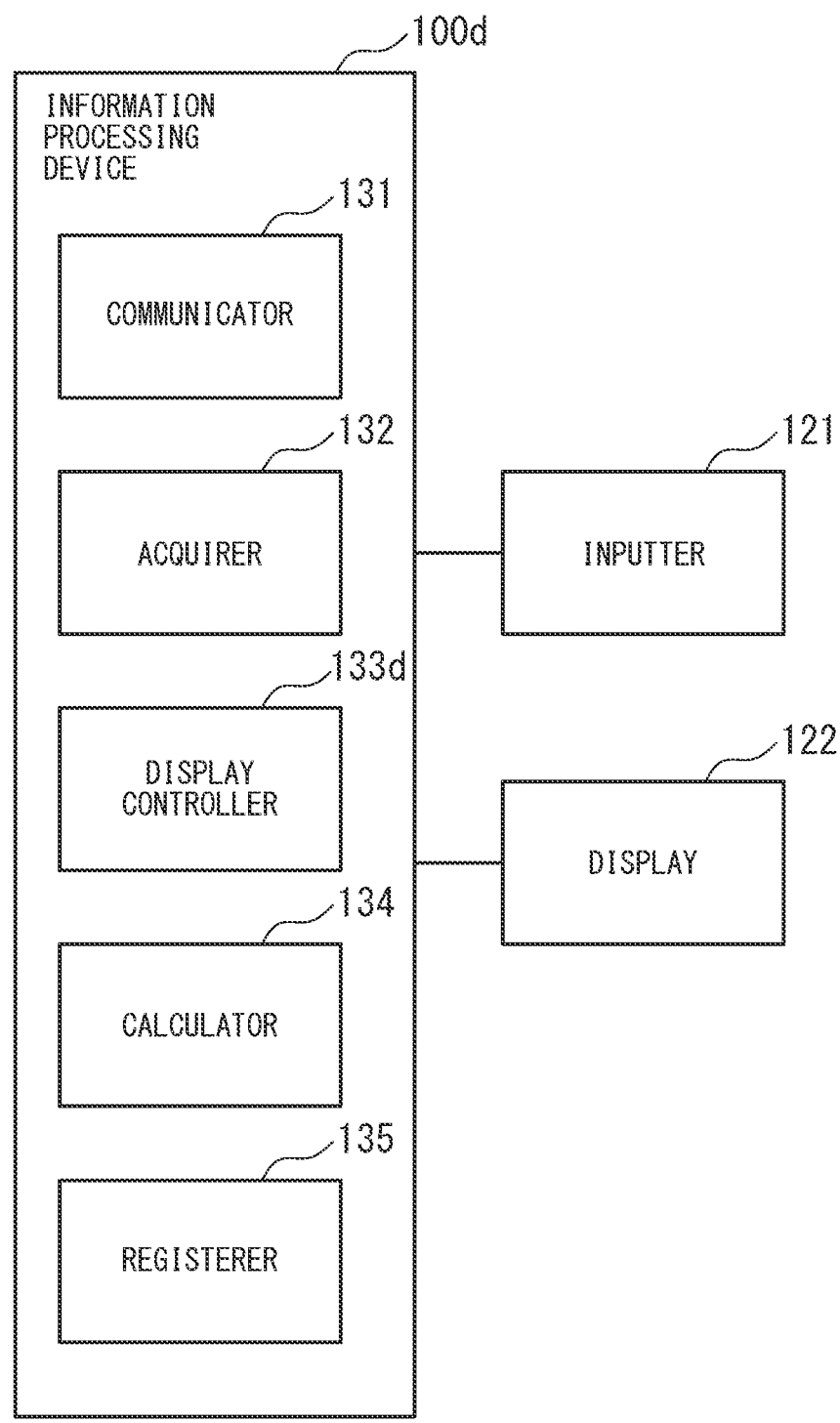
FIG. 35 is a block diagram showing a functional configuration example of an information processing device according to a fifth embodiment.

FIG. 35 is a block diagram showing a functional configuration example of an information processing device according to the fifth embodiment. As shown in FIG. 35, an information processing device 100d has a communicator 131, an acquirer 132, a display controller 133d, a calculator 134, and a registerer 135. An inputter 121 and a display 122 are connected to the information processing device 100d.

On a display image, the display controller 133d highlights storages of the container corresponding to a combination of functions specified by the user. For example, after having highlighted storages belonging to the same group with lines, a frame shape, and a color, the display controller 133d accepts the user's specification on functions. That is to say, after having confirmed observation results of a plurality of groups, the user further specifies functions in order to confirm storages corresponding to a function combination. In the present embodiment, regardless of the group (classification criterion), a process for confirming storages corresponding to any function combination is executed. The display controller 133d displays on the display 122 a display image that highlights storages corresponding to the specified function combination. The method of highlighting may be realized by at least one or more of using a color and added content. After storages have been highlighted, a group registration may be performed according to operations of the user if the group registration has not been done.

FIG. 36 is a diagram showing an example of a plate map according to the fifth embodiment. In FIG. 36, a case of applying the measuring application A and the measuring application B is taken as an example. As shown in FIG. 36, the display controller 133d displays a display image in which storages are highlighted on the plate map with a color or an added content according to the specified function combination. The storages shown in FIG. 36 are represented using effects for the sake of convenience of description, however, in reality, they would be represented in different colors. For example, storages with an anti-drying buffer fluid arranged on the outer side of the container is shown in gray on the display image. For example, storages represented with a grid effect in the container is shown in blue on the display image. As analysis information of observation results, the display image shows graphs indicating the number of target objects in storages in which the measuring application A and the measuring application B are combined. The display controller 133d shows the graphs also in blue (corresponding to storages with the grid effect).

Figure 37:
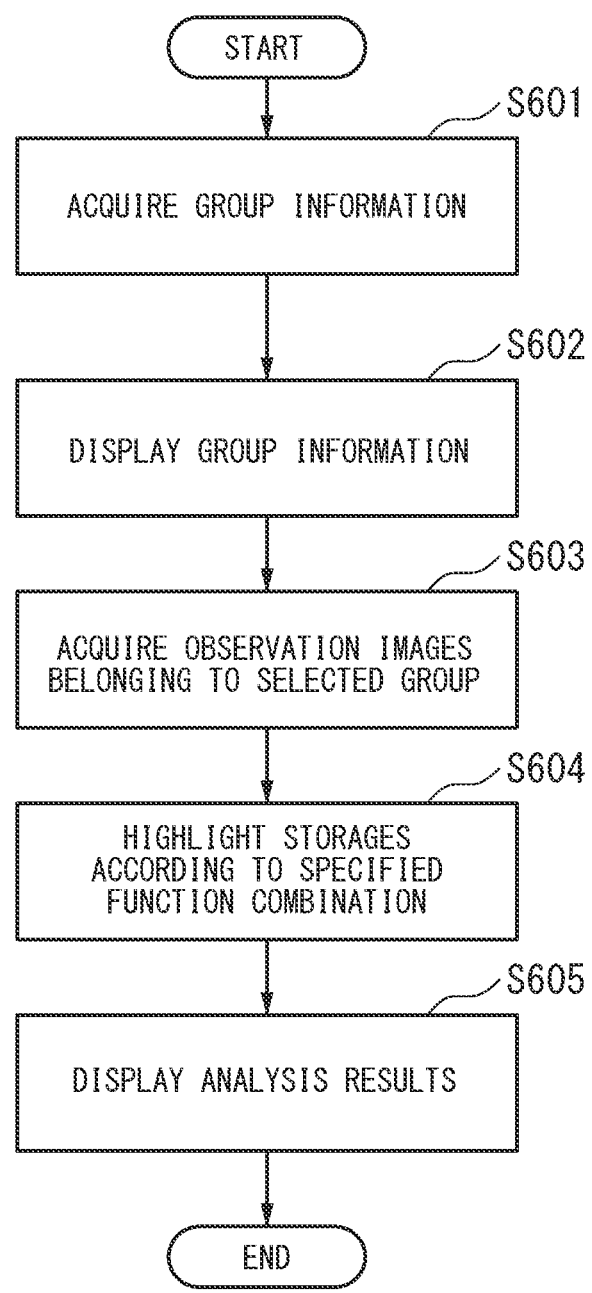
FIG. 37 is a flowchart showing an example of a flow of a process in the information processing device according to the fifth embodiment.

FIG. 37 is a flowchart showing an example of a process flow in the information processing device according to the fifth embodiment. In FIG. 37, the process flow in a situation where a plate map is being displayed is described. In Step S601, the acquirer 132 acquires from the memory storage device 110 information related to observation results of each group. In Step S602, the display controller 133d displays on the display 122 a display image including the information related to the observation results of each group acquired by the acquirer 132. Here, the user operates the inputter 121 to select an arbitrary group. The user may select a plurality of groups or select one group only.

In Step S603, the acquirer 132 acquires from the memory storage device 110 observation results including observation images that belongs to the group selected by the user. Here, the user operates the inputter 121 and specifies the function combination to be confirmed. In Step S604, the display controller 133d highlights the storages corresponding to the function combination specified by the user. In Step S605, the display controller 133d displays observation results. For example, the display controller 133d displays a display image that highlights the storages corresponding to the specified function combination, and that indicates the analysis results of observation results of the highlighted storages.

Sixth Embodiment

Hereunder, a sixth embodiment will be described. In the present embodiment, the same reference signs are given to configurations similar to those in the embodiment described above, and the descriptions thereof may be omitted or simplified in some cases.

Figure 38:
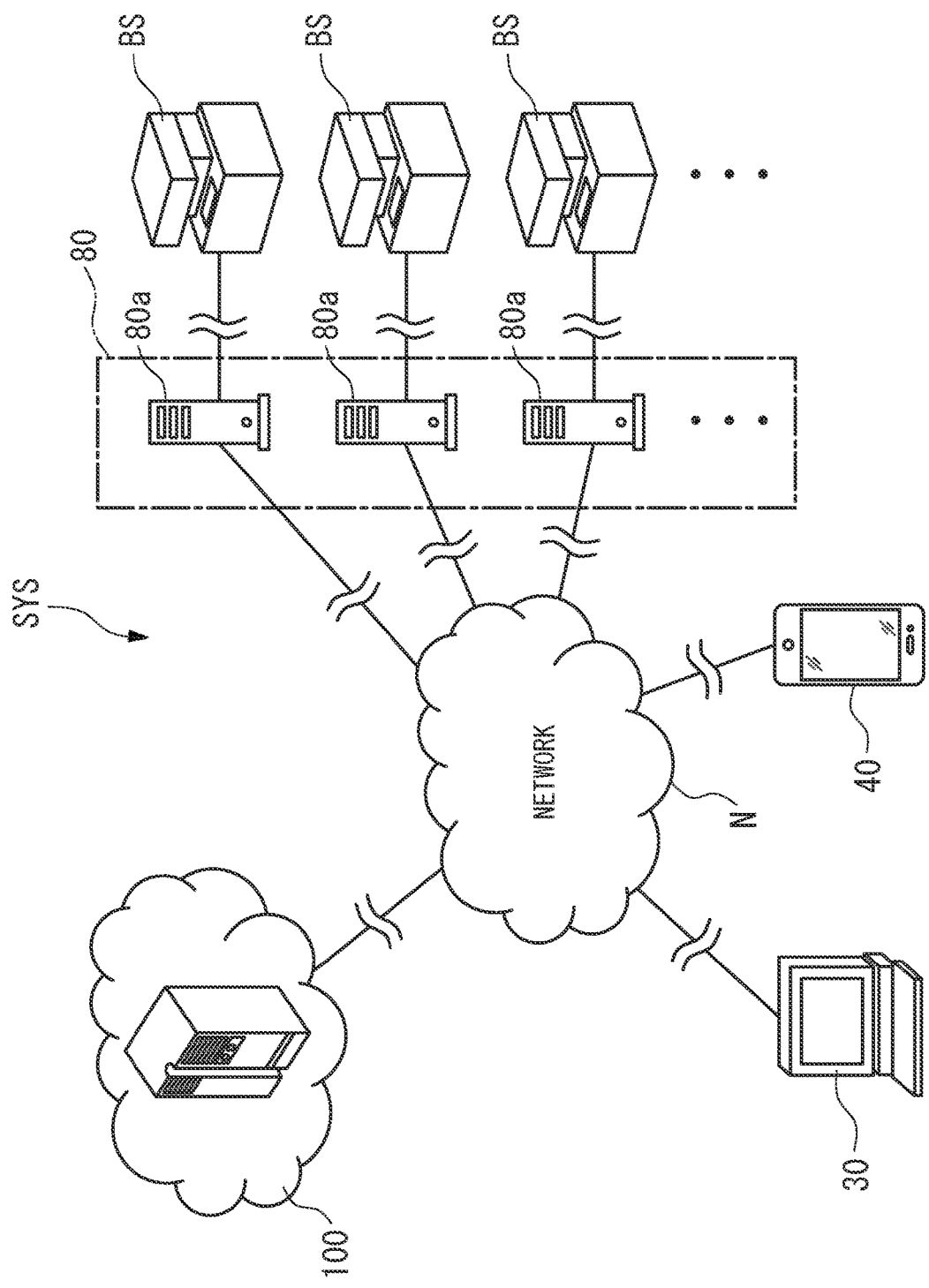
FIG. 38 is a diagram showing a configuration example of an information processing system according to a sixth embodiment.

FIG. 38 is a diagram showing a configuration example of an information processing system according to the sixth embodiment. As shown in FIG. 38, an information processing system SYS has a first terminal 30, a second terminal 40, a terminal device 80, an information processing device 100, and culturing systems BS. The first terminal 30, the second terminal 40, the terminal device 80, and the information processing device 100 are connected to each other so as to be able to communicate with each other via a network N. For example, the network N may be any of the Internet, a mobile communication network, and a local network, and may be a network in which networks of these several types are combined.

The terminal device 80 is composed of a plurality of gateway devices 80a. The gateway devices 80a are connected to the culturing systems BS in a wireless or wired manner. The information processing system SYS is configured such that a plurality of culturing systems BS are connected to the information processing device 100 via the terminal device 80, however, the invention is not limited to this example, and a single culturing system BS may be connected to the information processing device 100 via the terminal device 80. Furthermore, a plurality of information processing devices 100 or a single information processing device 100 may be provided in the information processing system SYS. Each information processing device 100 may include all of the various functions described in the above embodiments, or may include them in a distributed manner. That is to say, the information processing device 100 according to the present embodiment can be realized by cloud computing.

In the information processing system SYS, the user's terminal (such as first terminal 30 or second terminal 40) can connect to the information processing device 100, and observation results can be viewed or operated using a browser. As a server, the information processing device 100, in an acquirer, acquires observation results obtained by image-capturing a plurality of target objects stored in a container having a plurality of storages under predetermined observation conditions. Then, the information processing device 100 registers, in a registerer, two or more of the storages as the same group, based on the observation results and a classification criterion obtained from observation conditions or observation results. As a server, the information processing device 100, in the acquirer, acquires observation results obtained by image-capturing a plurality of target objects under predetermined observation conditions. On a display image related to a container having a plurality of storages respectively storing the plurality of target objects, the information processing device 100, as an image generator, highlights storages of the container that belong to a group meeting a classification criterion selected by the user of the user terminal (such as first terminal 30 or second terminal 40). Then, the information processing device 100, in an outputter, outputs the display image generated by the image generator to the user terminal via the network N.

In the embodiments described above, the information processing device 100 includes, for example, a computer system. The information processing device 100 reads an information processing program stored in a memory, and executes various processes in accordance with the read information processing program. Such an information processing program, for example, causes a computer to execute processes of: acquiring observation results obtained by image-capturing a plurality of target objects stored in a container having a plurality of storages under predetermined observation conditions; and registering two or more of the storages as the same group, based on the observation results and a classification criteria obtained from the observation conditions or the observation results. Furthermore, an information processing program, for example, causes a computer to execute processes of: acquiring observation results obtained by image-capturing a plurality of target objects under predetermined observation conditions; and highlighting, in a display image related to a container having a plurality of storages respectively storing the plurality of target objects, storages of the container that belong to a group meeting a classification criterion selected by a user. These information processing programs may be recorded and provided on a computer-readable memory storage medium (for example, a non-transitory memory storage medium, or a non-transitory tangible medium). In the embodiments described above, when displaying visually represented analysis results in a graph, the calculator 134 of the information processing device 100 may calculate a single set of data to be displayed in the graph (for example, data of horizontal axis in the graph) through calculation performed on a plurality of observation images (for example, integrating or averaging).

The technical scope of the invention is not limited to the aspects described in the above embodiments and so forth. One or more of the requirements described in the above embodiments and so forth may be omitted. The requirements described in the above embodiments may be combined where appropriate. Furthermore, the contents of all documents cited in the detailed description of the present invention are incorporated herein by reference to the extent permitted by law.

DESCRIPTION OF REFERENCE SIGNS

100: Information processing device
110: Memory storage device
121: Inputter
122: Display
131: Communicator
132: Acquirer
133: Display controller
134: Calculator
135: Registerer

The invention claimed is:

1. An information processing device comprising:
an acquirer that acquires observation results obtained by image-capturing a plurality of target objects under predetermined observation conditions; and
a display controller that highlights, with a first highlighting on a display image related to a container having a plurality of storages respectively storing the plurality of target objects, first storages of the plurality of storages that belong to a group meeting a classification criterion selected by a user,
wherein the display controller highlights, with a second highlighting on the display image and after having highlighted the storages that belong to the group meeting the classification criterion, second storages of the plurality of storages corresponding to an observation condition or an observation result specified by the user so that the first highlighting and the second highlighting are shown simultaneously on the same display image, and
wherein non-highlighted storages of the plurality of storages other than the first and second storages are also shown in the display image.

2. The information processing device according to claim 1,
wherein the display controller switches highlighting of the storages that belong to the group according to selection of the classification criterion.

3. The information processing device according to claim 1,
wherein the classification criterion is at least one of a type and an amount of a culture fluid to be charged into a storage of the plurality of storages.

4. The information processing device according to claim 1,
wherein the classification criterion is at least one of a type and a concentration of a serum included in a culture fluid to be charged into a storage of the plurality of storages.

5. The information processing device according to claim 1,
wherein the classification criterion is at least one of a type, a concentration, an exposure duration, and an exposure timing of a medicament to be charged into a storage of the plurality of storages.

6. The information processing device according to claim 1,
wherein the classification criterion is at least one of a type and a number of the target objects to be charged into a storage of the plurality of storages.

7. The information processing device according to claim 1,
wherein the classification criterion is at least one of a temperature setting, a humidity setting, an atmosphere supply setting, and a light output setting in a space in which the container is arranged.

8. The information processing device according to claim 1,
wherein the classification criterion is at least one of a number of, a temporal change in the number of, a doubling time of the number of, a movement amount of, and a form change in the target objects.

9. The information processing device according to claim 1,
wherein the display controller highlights, with a color, the storages of the plurality of storages that belong to the same group.

10. The information processing device according to claim 1,
wherein the display controller highlights, with a frame, the storages of the plurality of storages that belong to the same group.

11. The information processing device according to claim 1,
wherein the display controller adds and highlights, in a vicinity of the plurality of storages of the container, a content indicating the group to which the storages belong.

12. The information processing device according to claim 1,
wherein the display controller highlights, with a color, the storages of the plurality of storages that correspond to the same observation condition or the same observation result.

13. The information processing device according to claim 1,
wherein the display controller highlights, with a frame, the storages of the plurality of storages that correspond to the same observation condition or the same observation result.

14. The information processing device according to claim 1,
wherein the display controller adds and highlights, in a vicinity of the storages of the plurality of storages, a content indicating which of the observation conditions or the observation results it is.

15. The information processing device according to claim 1,
wherein after having highlighted the storages that belong to the group meeting the classification criterion, the display controller highlights storages of the plurality of storages according to a threshold value condition specified by the user, on the display image.

16. The information processing device according to claim 15, wherein the display controller adds a content for adjusting the threshold value condition to the display image.

17. The information processing device according to claim 1,
wherein after having highlighted the storages that belong to the group meeting the classification criterion, the display controller highlights storages of the plurality of storages corresponding to a combination of functions specified by the user, on the display image.

18. The information processing device according to claim 1,
wherein at least one storage of the plurality of storages is included in both the first and second storages, and
wherein at least one storage of the plurality of storages is not included in either the first storage or the second storage.

19. The information processing device according to claim 1,
wherein the first highlighting adds a first color to the first storages of the plurality of storages, and
wherein the second highlighting either (i) adds a second color to the second storages of the plurality of storages or (ii) adds a frame around the second storages.

20. An information processing method comprising:
acquiring observation results obtained by image-capturing a plurality of target objects under predetermined observation conditions;
highlighting, with a first highlighting on a display image related to a container having a plurality of storages respectively storing the plurality of target objects, first storages of the plurality of storages that belong to a group meeting a classification criterion selected by a user; and
highlighting, with a second highlighting on the display image and after having highlighted the storages that belong to the group meeting the classification criterion, second storages of the plurality of storages corresponding to an observation condition or an observation result specified by the user so that the first highlighting and the second highlighting are shown simultaneously on the same display image, and
wherein non-highlighted storages of the plurality of storages other than the first and second storages are also shown in the display image.

\* \* \* \* \*